Figure 1:
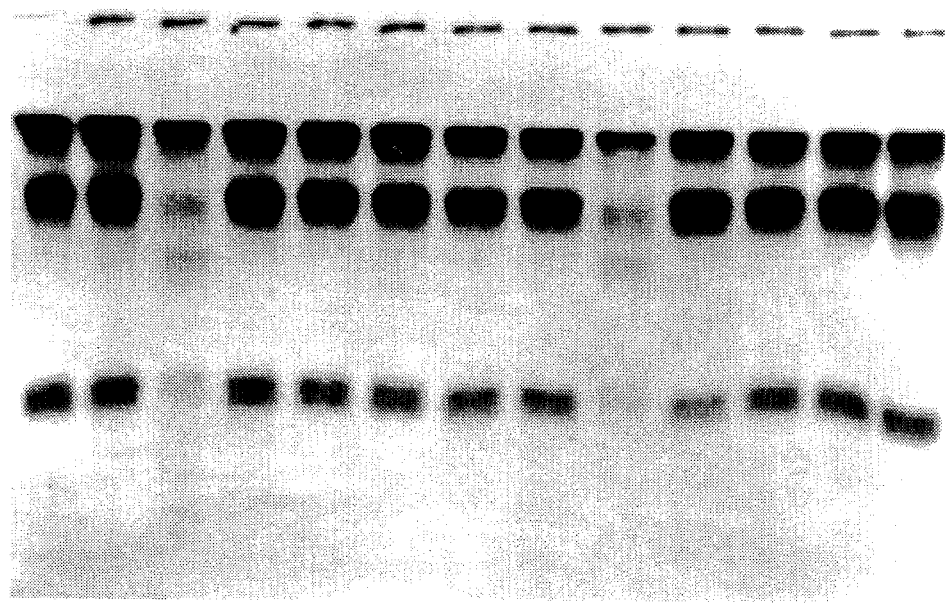

United States Patent [19]

Mellors et al.

[11] Patent Number: 5,543,312
[45] Date of Patent: Aug. 6, 1996

[54] PASTUERELLA HAEMOLYTICA GLYCOPROTEASE GENE AND THE PURIFIED ENZYME

[75] Inventors: Alan Mellors; Reggie Y. C. Lo, both of Guelph; Khalid M. Abdullah, Kitchener, all of Canada

[73] Assignee: University of Guelph, Ontario, Canada

[21] Appl. No.: 87,797

[22] PCT Filed: Jan. 15, 1992

[86] PCT No.: PCT/CA92/00019

§ 371 Date: Aug. 12, 1993

§ 102(e) Date: Aug. 12, 1993

[87] PCT Pub. No.: WO92/13078

PCT Pub. Date: Aug. 6, 1992

[30] Foreign Application Priority Data

Jan. 15, 1991 [GB] United Kingdom .................. 9100825

[51] Int. Cl.$^6$ ................... C12N 1/21; C12N 9/52; C12N 15/57; C12P 21/00
[52] U.S. Cl. ................... 435/220; 435/240.2; 435/252.3; 435/320.1; 536/23.2; 536/24.32
[58] Field of Search .................. 536/23.2, 24.32, 536/24.3; 435/252.3, 240.2, 320.1, 6, 220

[56] References Cited

U.S. PATENT DOCUMENTS

| | | | |
|---|---|---|---|
| 4,503,035 | 3/1985 | Pestka | 424/85.7 |
| 4,906,571 | 3/1990 | Mellors et al. | 435/220 |
| 5,082,785 | 1/1992 | Manning | 435/252.32 |

OTHER PUBLICATIONS

Proteolysis of Sialoglycoprotein by Pasteurella haemolytica Cytotoxic Culture Supernatant, Otulakowski et al, Infection and Immunity, vol. 42 (1983) pp. 64–70.

Neuraminidase Activity of Pasteurella haemolytica Isolates, Frank et al, Infection and Immunity, vol. 32 (1987) pp. 1119–1122.

Distribution of glycoprotease activity and the glycoprotease gene among serotypes of Pasteurella haemolytica, Abdullah, et al, Biochem. Soc. Transactions, vol. 18 (1990) pp. 901–903.

Vaccination of Calves with Leukotoxic Culture Supernatant from Pasteurella haemolytica, Shewen et al, Can. J. Veterinary Res., vol. 52 (1988) pp. 30–35.

Efficacy testing a Pasteurella haemolytica extract vaccine, Shewen, et al., Veterinary Med (Oct. 1988) pp. 1078–1083.

Cloning, Nucleotide Sequence, and Expression of the Pasteurella haemolytica A1 Glycoprotease Gene, Abdullah, et al., J. Bacteriol., vol. 173 (1991) pp. 5597–5603.

Cloning and Expression of the Leukotoxin Gene of Pasteurella haemolytica A1 in *Excherichia coli* K–12, Lo, et al., Infection and Immunity, vol. 50 (1985) pp. 667–671.

Wozney et al (1990) Meth Enzymol. 182, 738–749.

Sofer et al. (1983) Bio Techniques Nov./Dec., 198–203.

*Primary Examiner*—Robert A. Wax
*Assistant Examiner*—Eric Grimes
*Attorney, Agent, or Firm*—Bell, Seltzer, Park & Gibson, P.A.

[57] ABSTRACT

A purified DNA molecule encoding a glycoprotease from *Pasteurella haemolytica* is disclosed. The DNA comprises a sequence of approximately 975 base pairs coding for a glycoprotease having a molecular weight of approximately 35.2 kD. The glycoprotease is specific for cleaving O-glycosylated carbohydrate portions from O-glycoproteins. The glycoprotease has a major cleavage site in glycophorin A between Arg31 and Asp32.

10 Claims, 14 Drawing Sheets

1 kbp

FIG.4.-1

```
                                                    GGATCCAAGA ATATGAAAGC AAAGAGCTAC CGAATCCTGA
                                                              B
        -140       -130       -120       -110

AAAACTGAAG TATGGCGAAC AATTCTAGTC GTACAGAGAA TAATGTGACG GGCGTTCTTC GCCCTTTTG
  -100       -90       -80       -70       -60       -50       -40       -30

GTTTCTAAC TTATTTGAC TTCTCCAACT ATG CGA ATT TTA GGT ATT GAA ACC TCT TGT GAT
    -20       -10       1          Met Arg Ile Leu Gly Ile Glu Thr Ser Cys Asp
                                    10                  20                  30

GAA ACC GGT GTT GCC ATT TAT GAT GAA GAC AAA GGC TTA GTG GCA AAC CAG CTT TAT
Glu Thr Gly Val Ala Ile Tyr Asp Glu Asp Lys Gly Leu Val Ala Asn Gln Leu Tyr
         40                  50                  60                  70                  80                  90

AGC CAA ATT GAT ATG CAC GCC GAT TAC GGT GGC GTA GTC CCT GAA CTG GCT TCT CGA
Ser Gln Ile Asp Met His Ala Asp Tyr Gly Gly Val Val Pro Glu Leu Ala Ser Arg
         100                 110                 120                 130                 140

GAC CAT ATC CGT AAA ACG TTG CCA CTA ATT CAA GAA GCC TTA AAA GAG GCC AAT CTG
Asp His Ile Arg Lys Thr Leu Pro Leu Ile Gln Glu Ala Leu Lys Glu Ala Asn Leu
         150                 160                 170                 180                 190                 200
```

FIG.4-2

```
         210              220              230              240              250              260
          *                *                *                *                *                *
CAA CCC TCG GAT ATT GAC GGC ATT GCC TAT ACT GCC GGC CCA GGC TTG GTC GGG GCT
Gln Pro Ser Asp Ile Asp Gly Ile Ala Tyr Thr Ala Gly Pro Gly Leu Val Gly Ala 270              280              290              300              310
          *                *                *                *                *
TTA TTG GTC GGC TCA ACC ATT GCC CGT TCG CTG GCT TAT GCT TGG AAT GTT CCG GCA
Leu Leu Val Gly Ser Thr Ile Ala Arg Ser Leu Ala Tyr Ala Trp Asn Val Pro Ala 320              330              340              350              360              370
          *                *                *                *                *                *
TTG GGC GTT CAC CAT ATG GAA GGG CAT TTA CTT GCC CCA ATG TTG GAA GAA AAT GCC
Leu Gly Val His His Met Glu Gly His Leu Leu Ala Pro Met Leu Glu Glu Asn Ala 380              390              400              410              420              430
          *                *                *                *                *                *
CCT GAA TTT CCG TTT GTG GCA TTA TTG ATT TCA GGT GGA CAC ACC CAA CTG GTA AAA
Pro Glu Phe Pro Phe Val Ala Leu Leu Ile Ser Gly Gly His Thr Gln Leu Val Lys 440              450              460              470              480
          *                *                *                *                *
GTT GAC GGC GTT GGG CAA TAC GAA CTA CTC GGG GAA TCA ATT GAT GAT GCT GCC GGT
Val Asp Gly Val Gly Gln Tyr Glu Leu Leu Gly Glu Ser Ile Asp Asp Ala Ala Gly
```

FIG. 4-3

```
490        500        510        520        530        540
 *          *          *          *          *          *
GAA GCC TTT GAC AAA ACA GGC AAA CTA CTC GGT TTG GAT TAC CCT GCC GGT GTA GCG
Glu Ala Phe Asp Lys Thr Gly Lys Leu Leu Gly Leu Asp Tyr Pro Ala Gly Val Ala 550        560        570        580        590        600
 *          *          *          *          *          *
ATG TCA AAA TTA GCC GAA TCC GGC ACG CCA AAT CGT TTT AAA ACC TTC CCT CGT CCA ATG
Met Ser Lys Leu Ala Glu Ser Gly Thr Pro Asn Arg Phe Lys Thr Phe Pro Arg Pro Met 610        620        630        640        650        660
 *          *          *          *          *          *
ACC GAC AGA CCG GGA CTG GAT TTC AGT TTC TCC GGT TTA AAA ACC TTT GCT GCG AAT
Thr Asp Arg Pro Gly Leu Asp Phe Ser Phe Ser Gly Leu Lys Thr Phe Ala Ala Asn 670        680        690        700        710
 *          *          *          *          *
ACG ATT AAA GCC AAT CTT AAT GAA AAT GGT GAA CTC GAT GAG CAA ACC AAA TGC GAT
Thr Ile Lys Ala Asn Leu Asn Glu Asn Gly Glu Leu Asp Glu Gln Thr Lys Cys Asp 720        730        740        750        760        770
 *          *          *          *          *          *
ATT GCC CAC GCA TTC CAA CAA GCC GTG GTT GAT ACT ATT TTA ATT AAA TGC AAG CGA
Ile Ala His Ala Phe Gln Gln Ala Val Val Asp Thr Ile Leu Ile Lys Cys Lys Arg
```

FIG.4-4

```
       780            790            800            810            820            830
        *              *              *              *              *              *
GCG TTA GAG CAA ACC GGC TAT AAA CGC TTA GTA ATG GCA GGC GTA AGT GCC AAT
Ala Leu Glu Gln Thr Gly Tyr Lys Arg Leu Val Met Ala Gly Val Ser Ala Asn 840            850            860            870            880
        *              *              *              *              *
AAA CAA TTA CGA GCA GAC CTT GCG GAA ATG ATG AAA AAA TTA AAA GGC GAA GTA TTC
Lys Gln Leu Arg Ala Asp Leu Ala Glu Met Met Lys Lys Leu Lys Gly Glu Val Phe 890            900            910            920            930            940
        *              *              *              *              *              *
TAC CCT CGC CCA CAA TTT TGC ACT GAC AAC GGC GCA ATG ATT GCC TAC ACT GGC TTT
Tyr Pro Arg Pro Gln Phe Cys Thr Asp Asn Gly Ala Met Ile Ala Tyr Thr Gly Phe 950            960            970            980            990           1000
        *              *              *              *              *              *
CTT CGC TTA AAA ACG ATG AAC AAA CCG ACT TAA GC ATTAGCGTAA ACCCCGCTGG
Leu Arg Leu Lys Thr Met Asn Lys Pro Thr ---
```

FIG.4-5

```
         1010       1020       1030       1040       1050       1060       1070
           *          *          *          *          *          *          *
CTATGACCGA ATTACCACCG ATTAATTAAC CTTTCAAGCG GTGAAATTTC TTGTTAATTT TGCAAAAATT
                                            ──────────────────────▶

1080       1090       1100       1110       1120       1130       1140
           *          *          *          *          *          *          *
TAATCAAAAA TAACCGCTTG CTATATGATA GATTAAATTT ATGAATAATT ATGTAATTAG CCTACCTCCG 1150       1160       1170
           *          *          *
CACAGGAGCG TAGAAAACAT ATTCAAGCTG AATTC
                                 ─────
                                   E
```

FIG. 6.

```
              10          20          30          40          50
              *     *     *     *     *     *     *     *     *     *
Orfx   MRVLGIETSC DETGIAIYDD EKGLLANQLY SQVKLHADYG GVVPELASRD
       |||:|||||| |||| |||| ||| |:|||||:|| |||||||||| ||||||||||
Gcp    MRILGIETSC DETGVAIYDE DKGLVANQLY SQIDMHADYG GVVPELASRD 60          70          80          90         100
              *     *     *     *     *     *     *     *     *     *
       HVRKTVPLIQ AALKESGLTA KDIDAVAYTA GPGLVGALLV GATVGRSLAF
       |:|||:|||| :|||:|:|:  :||| |||||| |||||||||| |:|:|||||
       HIRKTLPLIQ EALKEANLQP SDIDGIAYTA GPGLVGALLV GSTIARSLAY 110         120         130         140         150
              *     *     *     *     *     *     *     *     *     *
       AWDVPAI PVHHMEGHLLAPM LEDNPPEFPF VALLVSGGHT QLISVTGIGQ
       ||:|||  |||||||||||| ||:|:|:||| |||| ||||| ||:.:.. ||
       AWNVPALGVH HMEGHLLAPM LEENAPEFPF VALLISGGHT QLVKVDGVGQ 160         170         180         190         200
              *     *     *     *     *     *     *     *     *     *
       YELLGESIDD AAGEAFDKTA KLLGLDYPGG PLLSKMAAQG TAGRFVFPRP
       |||||||||| |||||||||: ||||||||.  .:|||:|...  ||:||:|||
       YELLGESIDD AAGEAFDKTG KLLGLDYPAG VAMSKLAESG TPNRFKFPRP 210         220         230         240         250
              *     *     *     *     *     *     *     *     *     *
       MTDRPGLDFS FSGLKTFAAN TIRDN----G -TDDQTRADI ARAFEDAVVD
       |||||||||| |||||||||| ||:|:    . .||:||:.|| |:||::||||
       MTDRPGLDFS FSGLKTFAAN TIKANLNENG ELDEQTKCDI AHAFQQAVVD 260         270         280         290         300
              *     *     *     *     *     *     *     *     *     *
       TLMIKCKRAL DQTGFKRLVM AGGVSANRTL RAKLAEMMKK RRGEVFYARP
       |: |||||| |:|||||||| ||||||||:| ||:||||||| | ||||| ||
       TILIKCKRAL EQTGYKRLVM AGGVSANKQL RADLAEMMKK LKGEVFYPRP 310         320         330         340
              *     *     *     *     *     *     *     *
       EFCTDNGAMI AYAGMVRFKA GATADLGVSV RPRWPLAELP AA
       :|||||||| |:|| :|: :
       QFCTDNGAMI AYTGF LRLKT MNKPT
```

PASTEURELLA HAEMOLYTICA GLYCOPROTEASE GENE AND THE PURIFIED ENZYME

This invention relates to the cloning, sequencing and expression of DNA of a gene for *Pasteurella haemolytica* glycoprotease. The genetic information and expression products may be used in a variety of types of assays. The purified glycoprotease enzyme may be use in a variety of chemical and biochemical modifications of glycoproteins.

*P. haemolytica* is the principal microorganism associated with bovine pneumonic pasteurellosis, a major cause of sickness and death in feedlot cattle in North America. Martin et al. 1980. "Factors associated with mortality in feedlot cattle: The Bruce County beef cattle project." *Can.J.-.Comp.Med.*; Yates, W. D. G. 1982. "A review of infectious bovine rhinotricheitis, shipping fever pneumonia and viral-bacterial synergism in respiratory disease of cattle." *Can.J.-.Comp.Med. P. haemolytica* has been divided into sixteen serotypes base on soluble or extractable surface antigens. Biberstein, E. L. 1978. "Biotyping and serotyping of *Pasteurella haemolytica*." Methods Microbiol. Among the sixteen serotypes, serotype A1 is the predominant microorganism isolated from pneumonic lungs. Smith, P. C. 1983. "Prevalence of *Pasteurella haemolytica* in transported calves." *Am. J. Vet. Res.*; Yates, W. D. G. 1982. "A review of infectious bovine rhinotricheitis, shipping fever pneumonia and vital-bacterial synergism in respiratory disease of cattle." *Can. J. Comp. Med. P. haemolytica* A1 produces a number of antigens which are secreted into the culture supernatant during its growth. These antigens include a heat-labile cytotoxin specific for ruminant leukocytes, Shewen et al. 1988. "Vaccination of calves with leukotoxic culture supernatant form *Pasteurella haemolytica.*" *Can. J. Vet. Med.*, a serotype-specific outer-membrane protein, Gonzalez et al. 1986. "Cloning of Serotype-Specific Antigen form *Pasteurella haemolytica* A1." *Infect. Immun.*, a glycoprotease specific for sialoglycoproteins, Otulakowski et al. 1983. "Proteolysis of Sialoglycoprotein by *Pasteurella haemolytica* Cytotoxic Culture Supernatant." *Infect. Immun.* and neuraminidase Frank, G. H. 198. "Neuraminidase Activity of *Pasteurella haemolytica* Isolates." *Infect. Immun.* Vaccination of calves with bacterial-free culture supernatant form logarithmic phase cultures induces resistance to experimental challenge. and a vaccine based on the culture supernatant has been developed (Presponse™) Shewen et al. 1988. "Efficacy testing a *Pasteurella haemolytica* extract vaccine." *Vet.Med.*; Shewen et al. 1988. "Vaccination of calves with leucotoxic culture supernatant from *Pasteurella haemolytica.*" *Can.J.Vet.Med.*

The glycoprotease of *P. haemolytica* A1 is highly specific for O-glycosylated glycoproteins, so that proteins which lack extensive O-sialoglycopeptides residues are not cleaved by the glycoprotease. The best characterized glycoprotein substrate for the glycoprotease is glycophorin A from human erythrocytes. We have found that cleavage by the enzyme occurs either in situ on the surface of erythrocyte plasma membrane, or when the substrate glycoprotein is in solution. This enzyme is a neutral metallo-protease and is non-toxic to cultured mammalian cells including bovine pulmonary macrophages, bovine endothelial cells and erythrocytes Otulakowski et al. 1983. "Proteolysis of Sialoglycoprotein by *Pasteurella haemolytica* Cytotoxic Culture Supernatant." *Infect. Immun.* The role of the glycoprotease in pathogenesis and in the induction of an immune response is unknown. A homogeneous enzyme preparation for the glycoprotease is difficult to isolate by conventional biochemical techniques.

We have discovered and cloned a gene for the *P. haemolytica* glycoprotease. We have cloned, sequenced and expressed the gene. The expression product of the gene can be isolated to provide the glycoprotease in homogeneous form. The enzyme has restricted substrate specificity, which has a variety of chemical and biochemical uses in modifying glycoproteins. Such uses include, characterization of glycoproteins through specific sites of cleavage by the glycoprotease, the glycoprotease may be used to dissect components of the immune response by the select cleavage of surface molecules on immune cells. The glycoprotease may also be used to facilitate immunopurification of various types of cells by cleaving surface glycoproteins.

Accordingly, aspects of the invention are as follows:

1) The gene codes for the *P. haemolytica* enzyme, which has unique substrate specificity. As recorded previously, it cleaves the cell surface O-sialoglycoprotein glycophorin A, either in situ on the surface of human erythrocytes, or when the protein is free in solution. The major site of cleavage is the amide bond between the Arginine 31 and the Aspartate 32 residues. Minor site cleavage appear to be at the Ala7-Met8, Try34-Ala35, Glu60-Arg61, Ala65-His66 and His67-Phe68 amide bonds.

2) The enzyme cleaves other glycoproteins. The enzyme cleaves the human cell surface glycoproteins CD34 (primitive bone marrow stem cell antigen), CD43 (leukosialin/sialophorin), CD44 (hyaluronate receptor). and CD45 (leukocyte common antigen). Other cell surface glycoproteins of humans and other organisms are good substrates for the enzyme action.

3) The gene can be used to make recombinant enzyme free from other proteins of *P. haemolytica*, and this enzyme can be used to generate specific polyclonal or monoclonal antibodies. The antibodies are useful in the screening of other organisms which may make similar enzyme. The antibodies can be used to neutralize the enzyme action, to determine the roles of the enzyme in disease processes where the bacterium *P. haemolytica* is known to be involved, and to screen for involvement of this bacterium in diagnosis of infection.

4) The gene sequence may be used to make probes, DNA polynucleotides, which will hybridize with native DNA in other bacteria and will detect the occurrence of this or similar (homologous) genes in other bacteria.

5) The gene sequence has revealed extensive homology with an unknown gene of *Escherichia coli*, a gene called Orfx. The *E. coli* gene product may be a proteolytic enzyme with some resemblances to the *P. haemolytica* glycoprotease.

6) The enzyme can be used to generate novel biological products by the cleavage of O-sialoglycoproteins of natural origin. The cleavage of the human platelet and endothelial cell surface glycoprotein thrombomodulin, by the *P. haemolytica* glycoprotease, may be used to generate a soluble anticoagulant with potential uses in the treatment of blood clotting disorders, including DIC (disseminated intravascular coagulopathy).

Figure 2A:
Figure 2B:
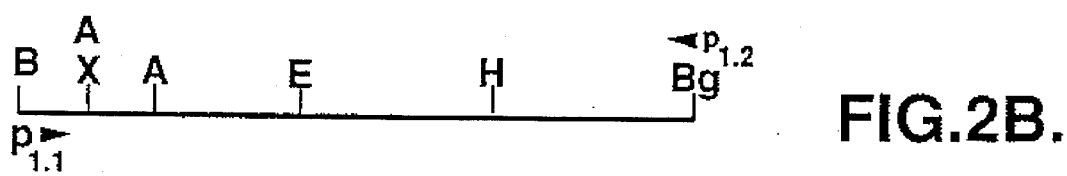

Various aspects of the invention are as follows:

1) A purified DNA molecule comprises a DNA sequence of approximately 975 bp coding for a glycoprotease having a molecular weight of approximately 35.2 kD, the DNA molecule having a restriction map of FIG. 2B.

2) A purified DNA molecule comprises the DNA sequence of FIG. 4 (SEQ ID NO:1) for bp positions 1 through 975.

3) A purified DNA molecule comprises at least 12 nucleotides selected from the group of nucleotides represented by bp positions 1 through 975 of FIG. 4 (SEQ ID NO:1).

4) A purified DNA molecule comprises a DNA sequence encoding a glycoprotease having an amino acid sequence of FIG. 4 (SEQ ID NO:1or 2).

5) A purified DNA molecule comprises at least 18 nucleotides encoding a fragment of a glycoprotease amino acid sequence, the fragment being selected from at least 6 corresponding sequential amino acid residues of the amino acid sequence of FIG. 4 (SEQ ID NO:1or 2).

6) A purified DNA probe comprises a DNA sequence of item 3.

7) A recombinant cloning vector comprises a DNA molecule of items 1, 2, 3, or 4.

8) A host is transformed with a recombinant cloning vector comprises a DNA molecule of items 1, 2, 3 or 4.

9) A method for screening a biological sample to determine presence of a gene encoding a glycoprotease of FIG. 4 (SEQ ID NO:1), comprises:
  i) providing a biological sample derived from a source suspected of a serotype of *P. haemolytica* which produces the glycoprotease,
  ii) conducting a biological assay to determine presence in the biological sample of at least a member selected from the group consisting of:
    a) glycoprotease gene sequence of FIG. 4 (SEQ ID NO:1), and
      b) glycoprotease amino acid sequence of FIG. 4 (SEQ ID NO:1or 2).

10) A purified glycoprotease protein produced by a host and isolated from culture of the selected cells, the protein having the amino acid sequence of FIG. 4 (SEQ ID NO:1or 2).

11) A purified glycoprotease protein fragment comprises at least six amino acid residues of the sequence of FIG. 4 (SEQ ID NO:1or 2).

12) An antibody specific for the glycoprotease.

13) A glycoprotease for cleaving glycoproteins which have portions rich in O-glycosylated carbohydrates, said glycoprotease having highly restricted specificity for cleaving solely said O-glycosylated carbohydrates portions from said glycoproteins, said glycoprotease being characterized by:
   i) a molecular weight of 35.2 kD,
   ii) cleaves glycophorin A at a major site between Arg 31-Asp 32 and at minor sites at least between Try 34-Ala 35, Glu 60 -Arg 61 and Ala 65-His 66,
   iii) a protein secreted from cultured *P. haemolytica* cells of selected serotypes 1, 2, 5, 6, 7, 8, 9 and 12, and
   iv) stable protease activity at pH 7.0–7.5.

14) A method for enzymatically cleaving only O-glycosylated carbohydrate portions from glycoproteins on cells surfaces, the method comprises treating cells having the glycoproteins rich in the O-glycosylated portions with the glycoprotease.

15) A cell having solely O-sialoglycosylated carbohydrate protein portions of glycoproteins in its cell wall enzymatically cleaved therefrom by treatment with the glycoproteins.

16) A vaccine comprises glycoprotease of item 14 and a pharmaceutically acceptable carrier for vaccine administration.

Aspects of the invention are demonstrated with respect to the drawings wherein:

FIG. 1. Glycoprotease activity in *E. coli* recombinant clones. Lanes: a, $^{125}$I-glycophorin A only; b, *E. coli* carrying pBR322; c, *E. coli carrying pPH1*; d, *E. coli* carrying pPHS; e through k are the other *E. coli* clones of the genomic library. $(GPA)_2$, glycophorin A dimer; GPA, glycophorin A monomer.

FIG. 2. Restrictions maps of plasmids used in this study. (A) Restriction map of insert DNA in pPH1 and pPH8. The arrows indicate the direction and extent of DNA sequenced. (B) Subcloning of 3.3-kpb BamHi-BglII fragment from pPH1 into pTTQ19 in either orientation. p, direction of expression from the tac promoter in pPH1.1 and pPH1.2; dark bars with ΔA and ΔE, internal fragments deleted in the plasmids pPH1.2A and pPH1.1E, respectively; open bar, open reading frame coding for gcp as deduced from the DNA sequence. Abbreviations: A, AvaI; B, BamHI; Bg, BglII; B/S, BamHI-Sau3A junction; E, EcoRI; H, HindIII; X, XbaI.

FIG. 3. Maxicell labelling of the plasmid-encoded proteins. Autoradiogram of 15% SDS-PAGE containing [$^{3}$S] methionine-labelled proteins expressed in *E. coli* carrying pBR322 (lane a), pPH1 (lane b), pPH1.1 (lane c), pPH1.2 (lane d), pPH1.1A (lane e), pPH1.1E (lane f), and pTTQ19 (lane g). The β-lactamase of pBR322 and the Lac repressor protein of pTTQ19 are indicated by Bla and I, respectively. Molecular size standards, starting from the top, represent 92.5, 66, 43, 31 and 21 kDa. The solid circles in the gel show the position of the 53-kDa protein corresponding to the glycoprotease.

FIG. 4. Nucleotide sequence (SEQ ID NO:1) of insert DNA between the BamHI and EcoRI sites in pPH1.1. The numbers above each line refer to nucleotide positions, which are arbitrarily numbered from −140 at the BamHI site to 1170 at the EcoRI site. The predicted amino acid sequence for the glycoprotease is shown beneath the DNA sequence (SEQ ID NO:2). The inverted repeats downstream from the gcp translational stop codon are underlined with arrows. Abbreviations: B, BamHI; E, EcoRI.

FIG. 5. Hydropathy profile of the glycoprotease protein. The method used was that of Klein, P., M. Kanehisa and C. DeLisi. 1985. The Detection and Classification of Membrane-Spanning Proteins. *Biochem. Biophys.* Acta. 815:468–476. The vertical axis gives the scale of the hydrophobic (positive) and hydrophilic (negative) values established for each window of nine residues. The horizontal axis gives the scale for the amino acids in protein.

FIG. 6 Homology between the glycoprotease (SEQ ID NO:2) and OrfX (SEQ ID NO:3). The segmented vertical lines show the location of identical residues. The segmented horizontal lines represent repressor breaks introduced to maximize homology. Potential zinc ligand of the glycoprotease and OrfX at His-111 and His-115 is underlined.

FIG. 7. High-level expression and secretion of the glycoprotease. (A) Total cellular proteins expressed from cultures of *E. coli* HB101 carrying pTTQ18 (lane 1), uninduced pGP1 (lane 2), pTTQ18 (lane 3), and pGP1 induced with IPTG (lane 4) separated by 15% SDS-PAGE and stained with Coomassie blue. The glycoprotease protein is indicated by an arrowhead. (B) Periplasmic fractions after osmotic shock treatments to *E. coli* HB101 carrying induced pGP1. Lane 1, Cytoplasmic fraction; lane 2, periplasmic fraction. Molecular size standards are in kilodaltons.

FIG. 8. Enzyme activity of the highly expressed glycoprotease in *E. coli* HB101. Lane a, $^{125}$I-glycophorin A only; lane b, negative control, protein extract from *E. coli* carrying pTTQ18; lane c, positive control, concentrated culture supernatant of *P. haemolytica* A1; lane d, protein extract from E. coli carrying. pGP1 after IPTG inductions. $(GPA)_2$, glycophorin A dimer; GPA, glycophorin A monomer.

FIG. 9. Autoradiographs of SDS-PAGE gels showing hydrolysis of [$^{125}$I]-glycophorin A. A: Lane (a) [125I]-glycophorin A (20 µCi per mg), 1.7 per lane; lane (b) glycophorin A incubated with P. haemolytica A1 pH 4.5 fraction, 0.3 mg protein in 67 µl 0.1M HEPES buffer, pH 7.4, for 30 min; lane (c) 1.7 µg [$^{125}$I]-glycophorin A after desialylation with neuraminidase; lane (d) desialated glycophorin A incubated with P. haemolytica A1 fraction for 30 min; lane (e) glycophorin A incubated with P. haemolytica A1 fraction in the presence of 100 mM EDTA; lane (f) glycophorin A incubated with P. haemolytica A1 fraction, treated with 100 mM EDTA and then dialyzed overnight prior to incubation with substrate. B: Hydrolysis of 1.7 µg [$^{125}$I]-glycophorin A by P. haemolytica A1 culture supernatants (0.3 mg protein, pH 4.5 fraction) in HEPES buffer as above, over 80 min. The incubation are: lane (a) no incubation; lane (b) 5 min; lane (c) 10 min; lane (d) 20 min; lane (e) 40 min; lane (f) 80 min. $A_2$ is glycophorin A dimer, A is glycophorin A monomer.

Figure 10:
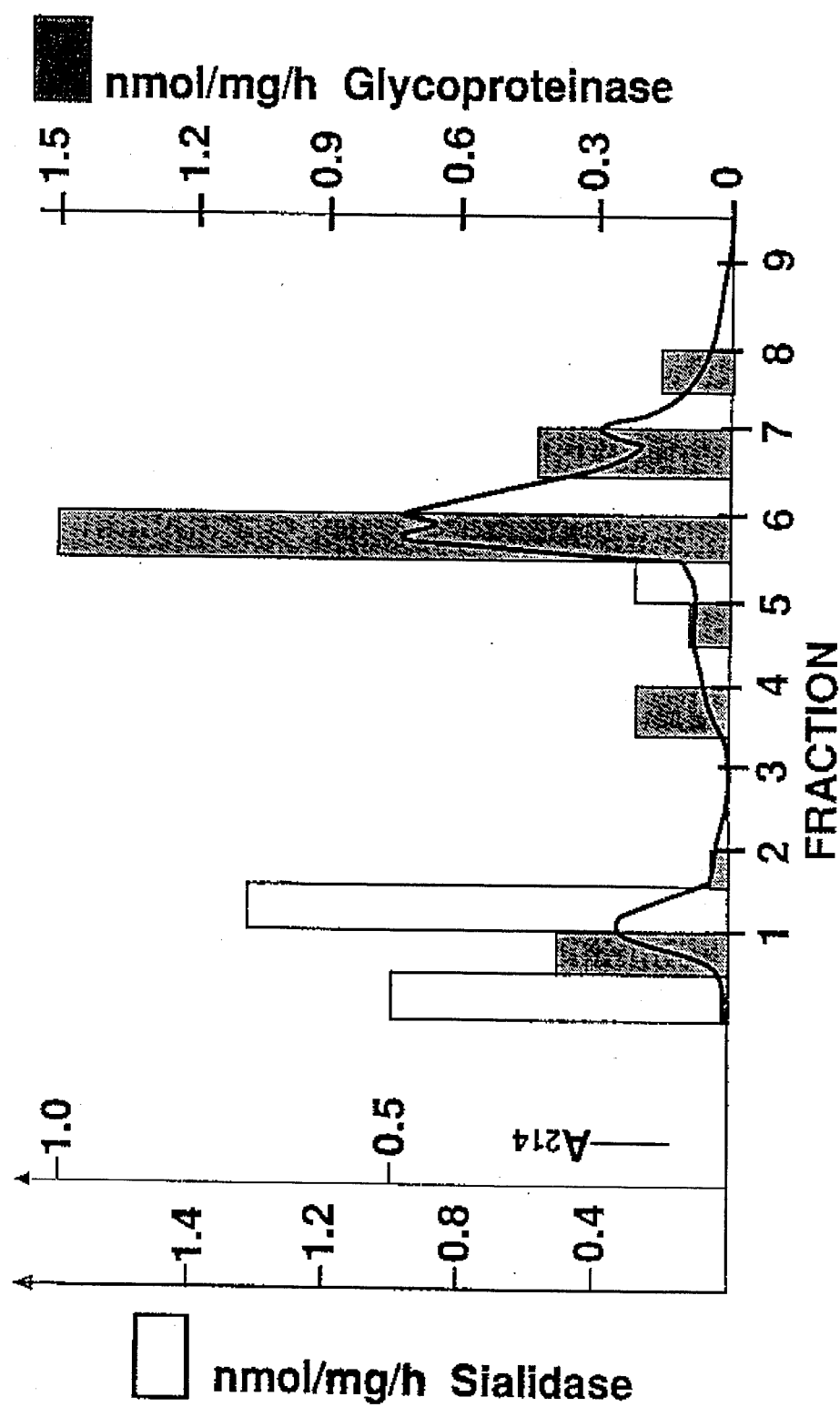

FIG. 10. Gel filtration HPLC separation of P. haemolytica A1 culture supernatant proteins. Serum-free culture supernatant was concentrated by ultrafiltration, with a 10 kD membrane pore size, to yield 100 µg of protein, which was chromatographed in Tris-HCl buffer, 0.1M pH 7.4, through two TSK G4000-SW molecular sieving columns 60 cm×0.75 cm, coupled in series, separation range 5–1000 kD. Elution was at 1 ml per min and six ml fractions were collected for glycoproteinase activity determination by the cleavage of [$^{125}$I]-glycophorin A (shaded bars) and neuraminidase activity determination by the cleavage of the fluorogenic substrate (open bars), with monitoring of protein absorbance at 214 nm (solid line).

Figure 11A:
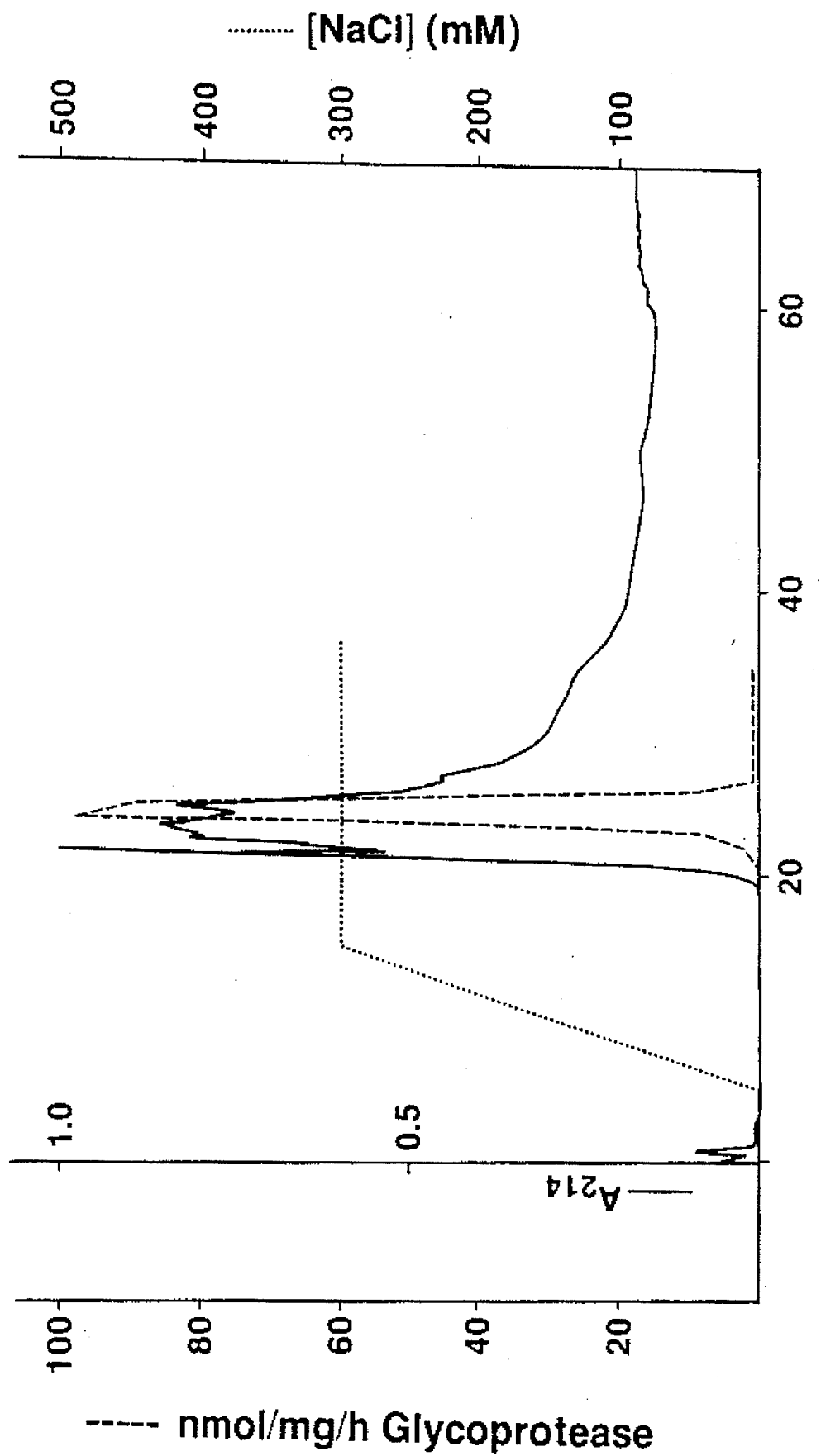
Figure 11B:
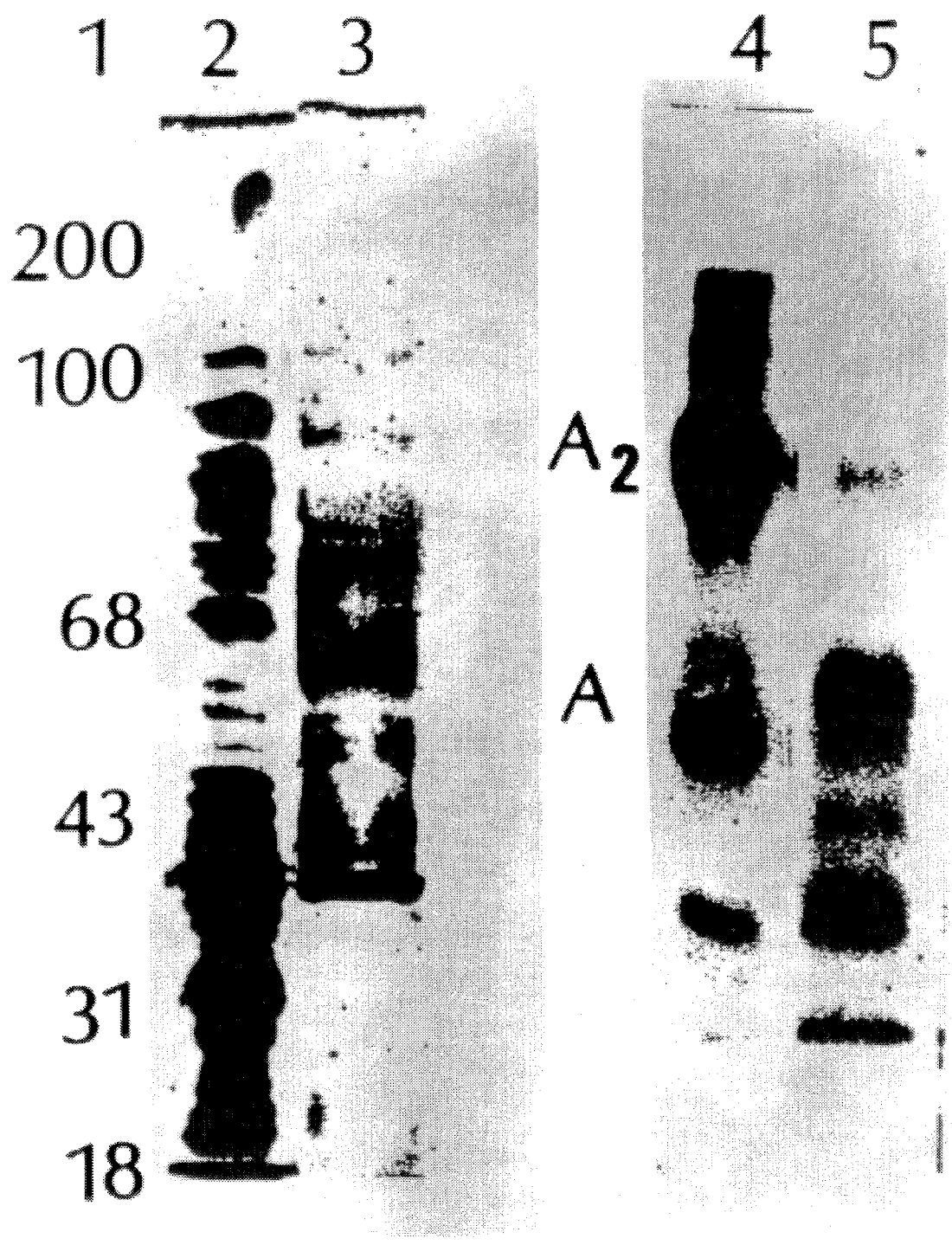

FIG. 11. (A) Anion exchange HPLC of fraction 6, from TSK columns. Fraction 6 (six mil) from the gel exclusion HPLC shown in FIG. 10, was concentrated by ultrafiltration, 10 kD membrane pore size, to yield 28.8 µg of protein. Twenty µg of this protein was chromatographed on a Mono Q HR 5/5 column and 1.0 ml fractions were eluted at 0.5 ml/min in Tris-HCL buffer, 0.1M pH 7.4, by a gradient of 0.0 to 0.5M NaCl. (B) SDS-PAGE analysis of fractions eluted from Mono Q column. (Lane 1) Molecular weight markers; Lane (2) Total proteins in the starting material, serum-free culture supernatant; (Lane 3) Fraction 24; (Lane 4) 1.7 µg [$^{125}$I]-glycophorin A substrate in 67 µl HEPES buffer pH 7.4; (Lane 5) glycophorin A as in lane 4, but incubated with 133 µl fraction 24 for one hour. Lanes 1–3 were visualized by silver-staining, and lanes 4 and 5 by autoradiography.

The discovery of the gene sequence (SEQ ID NO:1) which encodes for the P. haemolytica glycoprotease provides a number of significant advantages in the detection, molecular assays, protein mechanisms and medical care related to diseases caused by P. haemolytica infection and the uses of enzyme in cleaving glycoproteins and in particular O-sialoglycoproteins. Various DNA probes can be developed from the sequence (SEQ ID NO:1) described for purposes of detecting complementary DNA sequences in various types of biological materials including living cells. Portions of or the entire sequence (SEQ ID NO:1) may be expressed in an appropriate expression vehicle, which may be bacterial cells, viruses, plant, animal and in particular mammalian cells. The glycoprotease as produced by the expression of the DNA, or fragments of the enzyme as produced by corresponding fragments of the DNA may be used to perform various cleaving operations on molecules or other biological matter including living cells which have surface proteins including O-sialoglycoproteins. Expression of the selected DNA sequence in a transformed expression system provides purified enzyme, although it is appreciated the enzyme may be purified from culture of the selected P. haemolytica serotype. The produced protein may be used to develop various poly and monoclonal antibodies which are effective in diagnosis and various types of assays as well as potential uses in passive vaccines. The protein may also be used directly in various forms of animal vaccines in the treatment of P. haemolytica infections and in particular in combination with the vaccines disclosed in applicant's co-pending applications Ser. No. 786,662,720,332 and 462,929. There are of course other uses of the enzyme which have already been described or shall be described in the following description of this invention.

The cloning of the glycoprotease gene may be achieved in accordance with the following manner, employed by the inventors in discovering the gene.

The lysates from twenty-seven recombinant clones in E. coli were assayed for glycoprotease activity. The results in FIG. 1 shows an autoradiograph of the hydrolysis of radioiodinated glycophorin A incubated with lysate from clone pPH1. A negative control of the pBR322 transformed E. coli shows no hydrolysis, and a positive control of P. haemolytica A1 culture supernatant shows complete hydrolysis. Prolonged autoradiography of the gel also showed weak hydrolysis of $^{125}$S-glycophorin A by the lysate from another clone pPHS. The activity in pPH1 and pPH8 was 50% and 10% respectively of the glycoprotease activity of the culture supernatant sample from P. haemolytica A1. Restriction endonuclease analysis of the recombinant plasmids pPH1 and pPH8 showed that both plasmids contain an identical insert (FIG. 2), and pPH1 was chosen for further studies.

Figure 3:
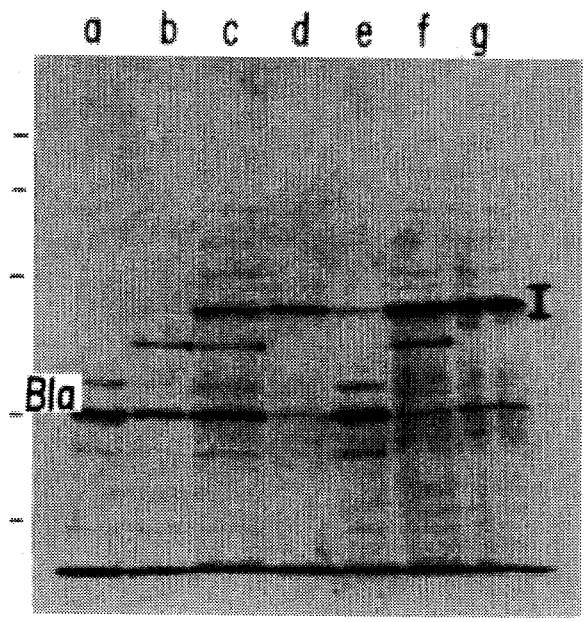
Figure 2C:
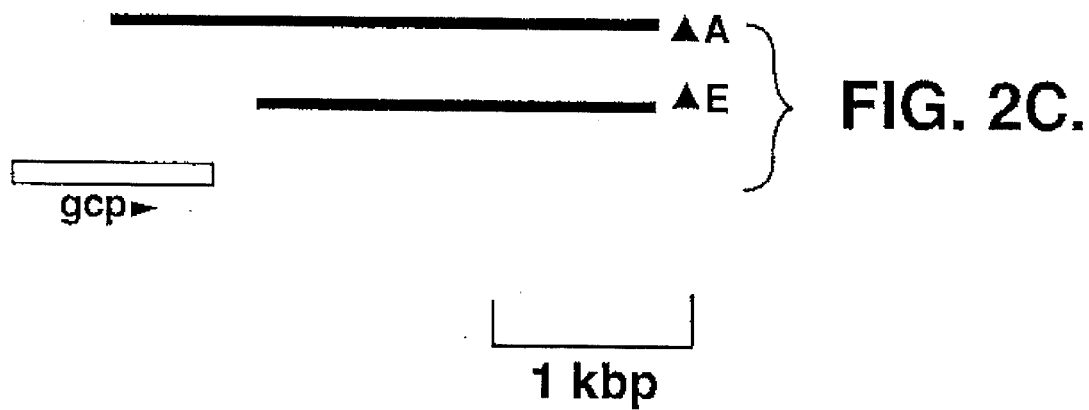

The plasmid pPH1 was transformed in E. coli CSR603 and the plasmid-encoded proteins examined by in vivo $^{35}$S-labelling. The results show that an additional protein of about 35 KD was expressed from pPH1 (FIG. 3). This gives an estimate of the size of the glycoprotease and is consistent with the estimated size of the enzyme, in SDS-PAGE analysis of extracts of P. haemolytica A1 culture supernatant. To locate the coding region of the glycoprotease gene on pPH1, the 3.3 kbp BamHI-BglII fragment was subcloned into the expression vector pTTQ19 to produce the subclones pPH1.1 and pPH1.2 which carry the insert DNA in opposite orientations (FIG. 2B). The plasmid-encoded proteins from pPH1.1 and pPH1.2 were examined in the E. coli maxi-cell system and the results are shown in FIG. 3. Only plasmid pPH1.1 expressed a plasmid-encoded protein identical in size to the cloned protein expressed from pPH1, suggesting that this plasmid encodes the correct orientation for expression. Two subclones were constructed from pPH1.1 by deleting selective internal fragments to yield the constructs pPH1.1A and pPH1.1E (FIG. 2C). Subclone pPH1.1A (constructed by partial digestion of pPH1.1 with AvaI and relegation) did not express the 35 kD protein whereas pPH1.1E still expresses the protein similar to that observed in pPH1 and pPH1.1 (FIG. 3). This showed that AvaI site is located within the glycoprotease gene and the EcoRI site may be close to the end of the gene. Based on the size of the glycoprotease expressed from the maxi-cell analysis, a DNA fragment of about 1 kbp is required to encode for this 35 kD protein and this gene must be located within the 2.3 kbp BamHI-HindIII fragment in the orientation depicted in pPH1.1.

The complete nucleotide sequence of the 2.3 kbp BamHI-HindIII fragment was determined and the 1.3 kbp sequence between the BamHI and EcoRI site is presented in FIG. 4 (SEQ ID NO:1). More than 80% of both strands of the DNA were sequenced either directly, or by the use of overlapping deletions of the cloned DNA, in the phage vectors M13 mp18 or M13 mp19. Most regions were sequenced at least three times independently in accordance with the procedure. Analysis of the DNA sequence revealed one large open reading frame expressing in the direction anticipated from the maxi-cell labelling experiments (FIG. 2). The open reading frame covers a length of 975 nucleotides and encodes for 325 amino acids with predicted molecular weight of 35.2 kD. These estimates are in agreement with size of the protein expressed in the maxi-cell labelling experiments. For purposes of further discussions, the gene encoding the glycoprotease is designated gcp.

The cloned glycoprotease was prepared from plasmid pGP1 (see below) as hereinafter described by SDS-PAGE and electroblotted onto PVDF membrane. The membrane region containing the glycoprotease was excised and the N-terminal amino acid sequence (SEQ ID NO:2) was determined. The results from the first eight cycles are identical to the first eight amino acids predicted from the nucleotide sequence of gcp and confirms the assignment of the reading frame for the glycoprotease.

An examination of the nucleotide sequence (SEQ ID NO:1) upstream from gcp did not reveal features similar to the promoter commonly found in *E. coli* (FIG. 4). Neither the consensus promoter sequences TATAAT nor the consensus RNA polymerase binding site TTGACA have been identified. Further, a putative ribosome-binding site immediately preceding the ATG initiation codon of gpc is also absent (FIG. 4). It is possible that the gcp promoter is not readily recognized in *E. coli* and this may explain the poor expression of glycoprotease activity in the initial clones pPH1 and pPH8. On the other hand, downstream from the termination codon of gcp, a mRNA structure consisting of a 14-bp stem and loop structure similar to the rho independent transcriptional signal of *E. coli* could be identified (FIG. 4). In two other loci sequences from *P. haemolytica*, sequences similar to the *E. coli* promoters can be identified, Lo et al. 1987. "Nucleotide Sequence of the Leucotoxin Genes of *Pasteurella haemolytica* A1." *Infect. Immun.*; Strathdee et al. 1989. "Cloning, nucleotide sequence, and characterization of genes encoding the secretion function of the *Pasteurella haemolytica* leukotoxin determinant." *J. Bacteriol.* As is understood, it is possible that different types of promoters under different regulatory systems are utilized in *P. haemolytica*.

Figure 5:
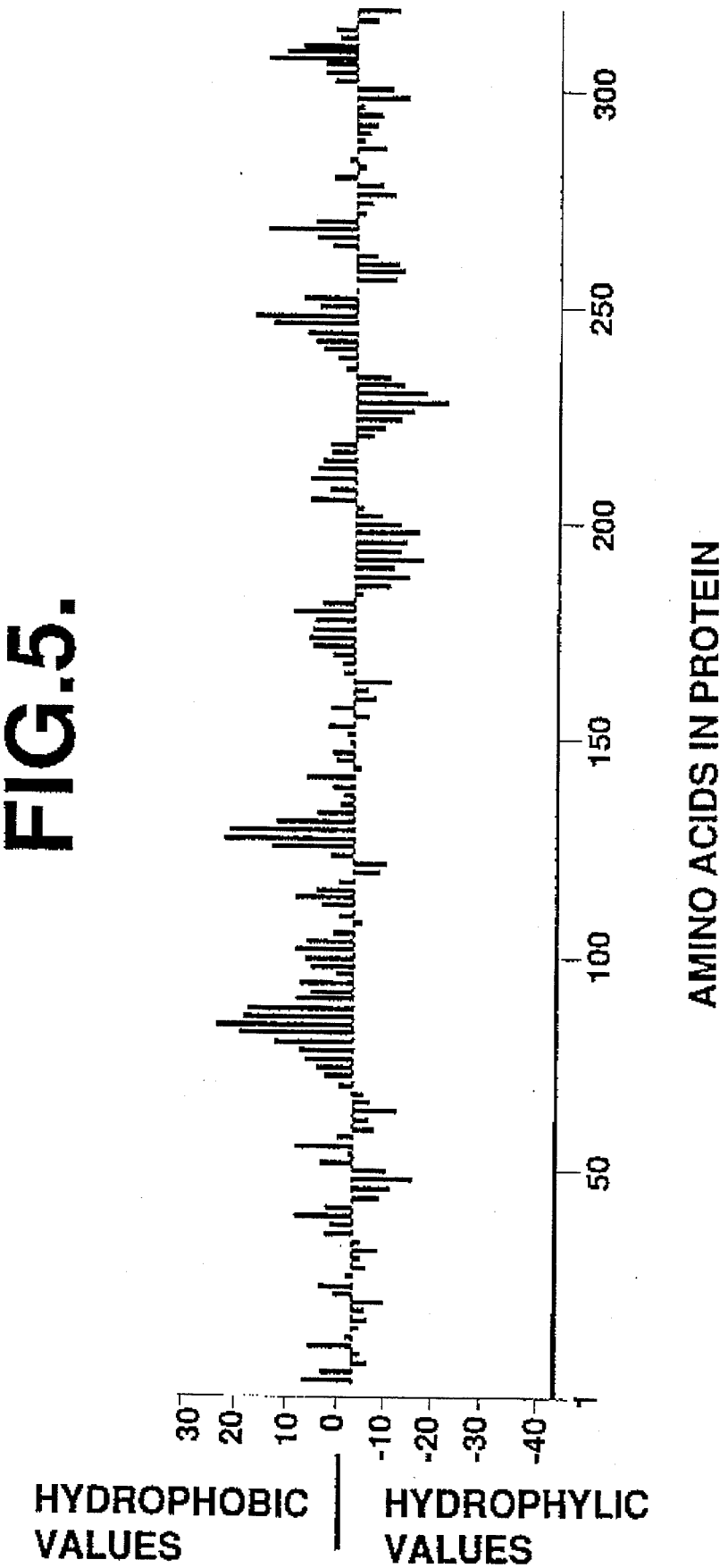

The predicted amino acid sequence (SEQ ID NO:2) of the glycoprotease was analyzed for its hydrophobicity and potential membrane spanning regions. FIG. 5 shows a hydropathy plot of the glycoprotease analyzed by the SOAP program (Klein et al supra). The analysis classified the glycoprotease as a potential peripheral membrane protein but not as an integral membrane protein with transmembrane domains. This is consistent with the glycoprotease found among the secreted products of *P. haemolytica* A1.

A search of the nucleotide sequence of gcp with databanks such as GenBank showed extensive homology with the DNA region upstream from the *E. coli* rpsU-dnaG-rpoD macromolecular-synthesis operon. In particular, gcp (SEQ ID NO1) is almost identical to an identified gene designated OrfX (SEQ ID NO:3) in that region Nesin et al. 1987. "Possible new genes revealed by molecular analysis of 5-kb *Escherichia coli* chromosomal region 5 to the rpsU-dnaG-rpoD macromolecular-synthesis operon." Gene. A comparison of the predicted amino acids of glycoprotease (SEQ ID NO:1) and OrfX (SEQ ID NO:3) is shown in FIG. 6. Almost 76% of the amino acids of glycoprotease are identical to those of OrfX, suggesting that the two proteins have similar functions. On the other hand, the codon usage in the two genes and the flanking nucleotide sequences are very dissimilar. Little is known about the function of the protein encoded by orfX except that it may be involved in regulation of expression of the rpsU-dnaG-rpoD operon, Nesin et al. 1987 (supra). However, based on this invention it is most likely that a proteolytic activity is associated with the OrfX protein, which may be part of the regulation of macromolecule biosynthesis.

Figure 7:
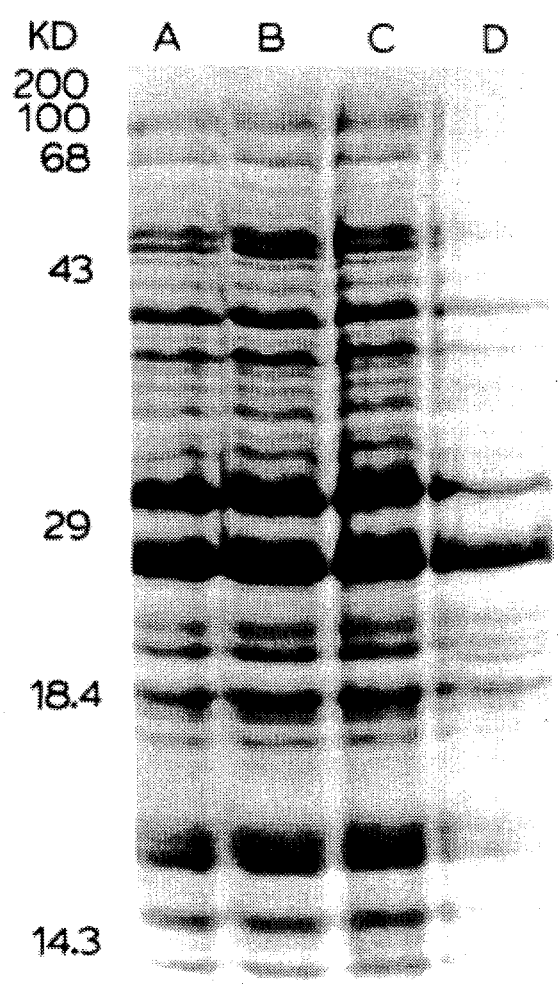
Figure 8:
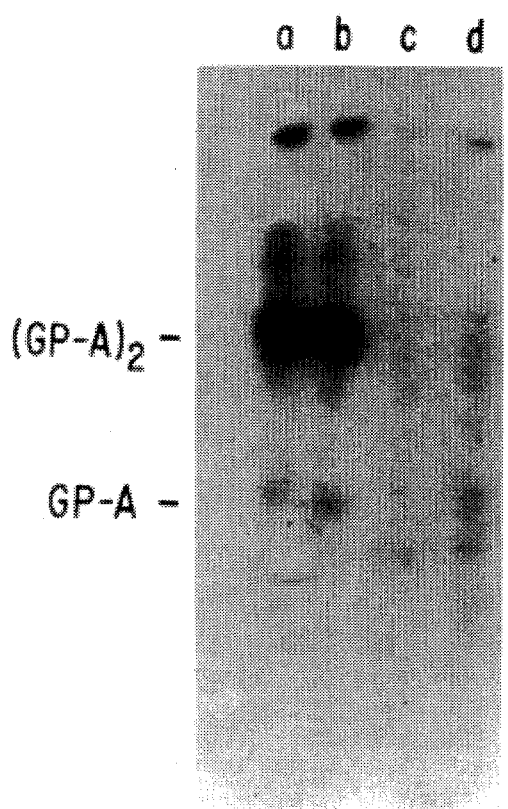

The 2.3 kbp BamHI-HindIII fragment was then subcloned into the BamHI and HindIII site of a high expression vector pTTQ18 to produce plasmid pGP1. This placed the initiation codon of gcp at an appropriate distance from the tac promoter to allow high expression of the glycoprotease. FIG. 7 shows expression of the *P. haemolytica* A1 glycoprotease in *E. coli* carrying pGP1, upon induction with IPTG (isopropyl-β-D-thiogalactoside). No glycoprotease could be detected in *E. coli* carrying only PTTQ18, nor in uninduced cultures (FIG. 7). The same protein preparations were also assayed for glycoprotease activity and the results in FIG. 8 showed that *E. coli* carrying pGP1 expressed enzyme activity identical to that found in the *P. haemolytica* A1 culture supernatant.

The overexpressed 35-kDa protein isolated by SDS-PAGE from *E. coli* lysates containing the glycoprotease activity was used to raise polyclonal antibody in rabbits. This antiserum was used to neutralize the glycoprotease activity in culture supernatants of *P. haemolytica* A1. Under conditions in which the *P. haemolytica* glycoprotease degraded 16.8 µg of glycophorin A in 30 min, when rabbit anti-glycoprotease antiserum was added at titers of ¼, ⅛, ⅟₁₆ and ⅟₃₂, degradation of glycophorin A dropped to 4.0, 8.9, 8.4, and 11.5 µg of glycophorin A per 30 min, respectively. Control antisera against 35-kDa bands from lysates of plasmid-transformed *E. coli* which lacked the pGP1 gene showed no inhibition of the *P. haemolytica* glycoprotease.

The glycoprotease of *P. haemolytica* A1 is normally secreted in the culture medium, but its mechanism of secretion is not known. After IPTG induction of *E. coli* carrying pGP1, the cells were subjected to osmotic shock treatment to determine the location of the glycoprotease. The glycoprotease is located in the periplasmic fraction of the *E. coli* clone. Only traces of the glycoprotease protein were detected in the cellular fraction. An examination of the DNA-derived N-terminal amino acid sequence of the glycoprotease (SEQ ID NO:2) showed the absence of a conventional signal peptide sequence. Furthermore, N-terminal amino acid sequence (SEQ ID NO:2) analysis of the glycoprotease expressed in *E. coli* showed that there is no cleavage of amino acids from the N-terminal region during export of the glycoprotease to the periplasm in *E. coli*. This suggests that there may be a different mechanism involved in the secretion of the glycoprotease.

The cloning and sequencing data show that the *P. haemolytica* A1 glycoprotease is a protein of 35.2 kD. The enzyme has a predicted pI of 5.2 which is consistent with our finding that the enzyme activity is precipitated from culture supernatants by lowering the pH to 4.5.

In the initial stages of developing expression of the gene, only low level of glycoprotease activity was expressed in *E. coli* transformed by pPH1 (or pPHS). This was most likely due to the inefficient activity of the *P. haemolytica* A1 gcp promoter in *E. coli* or to incomplete processing of the enzyme, or to instability of the enzyme in *E. coli*. Upon subcloning of the appropriate DNA fragment into pTTQ18, the level of glycoprotease activity in *E. coli* was increased, however, the specific activity of the enzyme preparation was less than that observed in serum-free culture supernatants of *P. haemolytica* A1. The lower specific activity of the recombinant product was probably due to a lack of post-translational processing of the cloned glycoprotease gene in *E. coli*.

The leukotoxin is another secreted protein of *P. haemolytica* A1, for which the nucleotide sequence and the regulation of leukotoxin expression has been described, Lo et al. 1987. "Nucleotide Sequence of the Leucotoxin Genes of *Pasteurella haemolytica* A1. "*Infect. Immun.*; Strathdee et al. 1989a, "Cloning, nucleotide sequence, and characterization of genes encoding the secretion function of the *Pasteurella haemolytica* leucotoxin determinant." *J. Bacteriol*; Strathdee et al 1989b. The leukotoxin determinant is composed of four contiguous genes lktCABD encoded on the same DNA strand where LktA is the structural gene for the leukotoxin (LktA), while proteins encoded by lktC functions in the activation of leukotoxin (LktA), while proteins encoded by lktB and lktD are involved in the secretion of leucotoxin. It possible that glycoprotease has a similar mode of activation as the leukotoxin, which could explain the lower specific activity of the enzyme expressed in *E. coli*. An examination of the amino terminus of the glycoprotease from pGP1 shows no pattern similar to the conventional signal sequences predicted for a number of secreted proteins characterized Michaelis et al. 1982. "Mechanism of incorporation of cell envelope proteins in *Escherichia coli.*" *Ann. Rev.*; Silhavy et al. 1988. "Mechanism of protein localization." *Microbiol. Rev.*; Von Heijne, G. 1983. "Patterns of amino acids near signal sequence cleavage sites." *Eur. J. Biochem*. Since the glycoprotease is normally secreted from *P. haemolytica* A1, an alternative secretory mechanism not involving an amino-terminus signal may be utilized, as reported for the leukotoxin, Strathdee et al. 1989. "Cloning, nucleotide sequence, and characterization of genes encoding the secretion function of the *Pasteurella haemolytica* leukotoxin determinant". *J. Bacteriol.*

It is therefore appreciated that with the variety of expression vehicles and expression systems and with the information provided by the gene sequence and the analysis of the corresponding protein sequence for the glycoprotease, manufacture of purified glycoprotease can be realized by those skilled in the art.

The glycoprotease of *P. haemolytica* A1 appears to have some similarity of action with other neutral metallo-protease of bacteria, such as thermolysin Nakahama et al. 1986. "Cloning and sequencing of Serratia protease gene." *Nucleic Acids Res*, but there is no major sequence homology with these enzymes, except for the presence of a potential zinc binding site (FIG. 6). The unusual substrate specificity for the glycoprotease, namely its specificity for O-sialoglycosylated proteins and the lack of homology with other known protease suggest that it is a member of a new enzyme class.

Prior to our discovery, little was known about the relationship between the glycoprotease of *P. haemolytica* A1 and other bacterial proteases. High level expression of pGP1 in *E. coli* upon induction with IPTG allows large scale preparation of the glycoprotease free from *P. haemolytica* A1 proteins. Such preparation can be used for detailed studies on the activities an immunological properties of the enzyme. Polyclonal antibodies are readily prepared in rabbits using the cloned enzyme. This is an important reagent for further characterization of biochemical and biological properties of the glycoprotease.

It is appreciated that with the protein sequence information for the glycoprotease, selected functional regions of the protein may be used in raising antibodies or the entire protein may be used in raising antibodies. In accordance with standard techniques the above-mentioned polyclonal antibodies may be developed, although it is understood that for particular applications monoclonal antibodies may be developed for diagnostic uses and the like. It is also appreciated that in the process of developing various forms of antibodies protein sequences normally of 6 residues or more would be selected.

It is also appreciated that the DNA sequence (SEQ ID NO:1) provides the necessary information to develop a variety of DNA probes which can be used in corresponding diagnosis. The probes can be developed from selected portions of the DNA sequence (SEQ ID NO:1) for purposes of determining the presence of certain functional portions of the sequence. It is generally understood that for purposes of DNA hybridization preferably 14 to 18 base pairs are selected. Such probes may be used to screen serotypes of *P. haemolytica* for the occurrence of the glycoprotease gene such as discussed in Abdullah et al. December 1990. "Distribution of glycoprotease activity and the glycoprotease gene among serotypes of *Pasteurella haemolytica*." Biochemical Society Transactions.

The glycoprotease was found to be unstable when isolated by HPLC from serum-free culture supernatants. However, alternative procedures for isolation and purification from culture are provided hereinafter. This is in marked contrast to the remarkable stability of the enzyme activity in freeze-dried pH 4.5 precipitates of culture supernatant, in which activity is maintained for many months at room temperature. The increased protein concentrations of the recombinant gene product expressed in highly active expression vectors should overcome the liability of the enzyme at low protein concentrations. The glycoprotease is only a minor protein component of the culture supernatant of *P. haemolytica* even in bacteria grown in serum-free media. Consequently it has been difficult to isolate a homogeneous preparation of the glycoprotease, except by laborious chromatographic methods. The recent identification of the recombinant glycoprotease as a 35 kD$^{35}$S-labelled band on SDS-PAGE, the high level of expression of this product, and the recognition that the recombinant product is located within the periplasmic space of *E. coli* HB101 enables one to obtain large amounts of highly purified product.

The best understood substrate for the glycoprotease other than the erythrocyte sialoglycoprotein is glycophorin, A Udoh et al. 1986. *Univ. of Guelph*. None of thirty proteins and glycoproteins tested previously was cleaved by the enzyme. When glycoproteins from various sources were radiolabelled with $^{125}$I-iodine and incubated with partially-purified enzyme, no hydrolysis of these substrates could be detected, by SDS-PAGE and autoradiography. No hydrolysis was seen for human immunoglobulin A1 (IgA1) or human immunoglobulin A2 (IgA2), so that the glycophorin-degrading enzyme is not identical to IgA protease, a microbial neutral metalloprotease Plaut et al. 1983. *Annu. Rev. Microbiol*. Similar procedures showed that the *P. haemolytica* protease does not degrade [$^{125}$I]-labelled bovine α-1 acid glycoprotein, bovine β-lactalbumin, or hen ovalbumin. The [$^{125}$I]-labelled proteins, bovine serum albumin, glyceraldehyde-3-phosphate dehydrogenase, soybean trypsin inhibitor, bovine carbonic anhydrase, trypsinogen and chymotrypsinogen were not cleaved by the *P. haemolytica* protease. Other proteins were tested as substrates by incubation with active enzyme fractions, and enzyme action was monitored by SDS-PAGE and Coomassie blue staining of the substrate products. The enzyme did not hydrolyze insulin chain A, insulin chain B, or cytochrome c. Partially purified enzyme preparations with high activity against glycophorin were inactive in cleavage of dye-casein conjugates (Azocasein) or dye-collagen conjugates (Azocoll). Thus the weak casein-degrading activity reported in culture supernatants of *P. haemolytica* Otulakowski et al. 1983. *Infect. Immun.* was not found in the glycoproteinase-enriched extracts used here.

The removal of sialyl residues from glycophorin, by treatment with neuraminidase destroys the susceptibility of the glycoprotein to hydrolysis by the enzyme. The high degree of specificity for an O-linked sialoglycoprotein, of a type commonly found on mammalian cell surfaces, is a unique property of this enzyme. Our results suggest that a major cleavage of glycophorin A occurs at the Arg31-Asp32 and this has been confirmed by N-terminal analysis of the one product, but there are other sites of cleavage. These other sites are in the glycosylated N-terminal region close to the O-linked sialoglycosylated residues which were noted above.

The glycoprotease activity is stable at pH 7.0–7.5, but is destroyed rapidly above pH 8.0. The enzyme can be inhibited by prolonged treatment (24h) with phenanthroline, so that it was tentatively classified as a neutral metallo-protease Otulakowski et al. 1983. *Infect. Immun.* EDTA is a poor inhibitor, unless the enzyme is prepared and assayed in serum-free media. Some inhibitions are given by millimolar concentrations of the acidic amino acids aspartate and glutamate but not by their amide analogues. The anions citrate, ascorbate and phosphate give similar inhibition, but sialate does not. The inhibition probably arises from competition between anions and the sialoglycoprotein substrates, in binding to the enzyme. It is unlikely that the inhibition by these anions is due to chelation of essential divalent metal cations by the inhibitor, since EDTA is a relatively weak inhibitor compared to citrate, ascorbate, aspartate, glutamate, and phosphate. The EDTA-inhibited *P. haemolytica* glycoprotease activity could not be reactivated by the addition of metal ions. Phosphoramidon [N-(β-L-rhamnopyranosyl-oxyhydroxy-phosphinyl-L-leucyl-L-tryptophan] is a potent inhibitor of neutral metallo-proteases such as thermolysin Malfroy et al. 1985. *Biophys. Res. Commun.* but without significant effect on the *P. haemolytica* protease. Lack of inhibition by phosphoramidon is consistent with the inability of the enzyme to hydrolyze the thermolysin substrate, furoylacryloylglycylleucinamide Otulakowski et al. 1983. *Infect. Immun.* The protease is not as heatstable as is thermolysin. There are several O-sialoglycoproteins, found on human cell surfaces, which are substrates for the *P. haemolytica* glycoprotease. These new substrates are well characterized leukocyte antigens with diverse functions. The enzyme thus provides a new tool with which to study the structure-function relationships for some cell surface antigens.

It is appreciated that the glycoprotease may also be produced by isolating and purifying the enzyme from a culture of a suitable strain of *P. haemolytica*. There are several serotypes which produce the glycoprotease. As we reported in (Abdullah et al. supra), *P. haemolytica* serotypes 1, 2, 5, 6, 7, 8, 9 and 12 secrete the glycoprotease. For purposes of understanding such isolation and purification steps and further understanding the purified glycoprotease, the following discussion is provided.

Figure 9B:
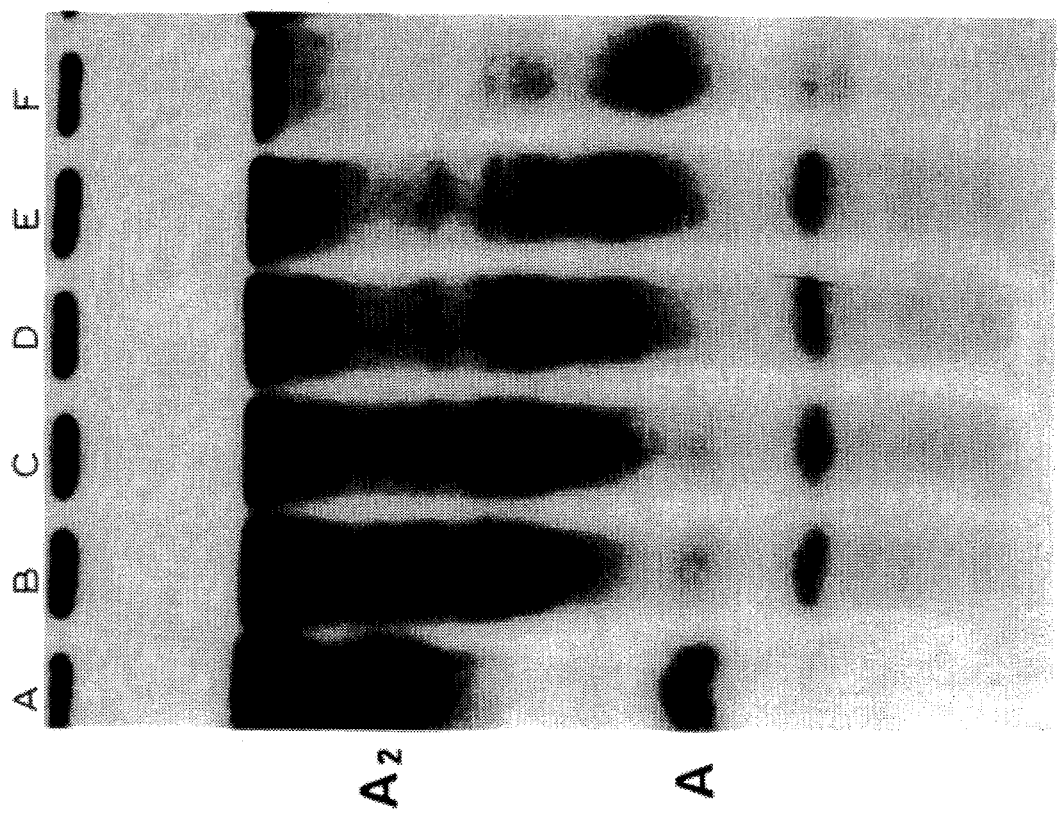
Figure 9A:
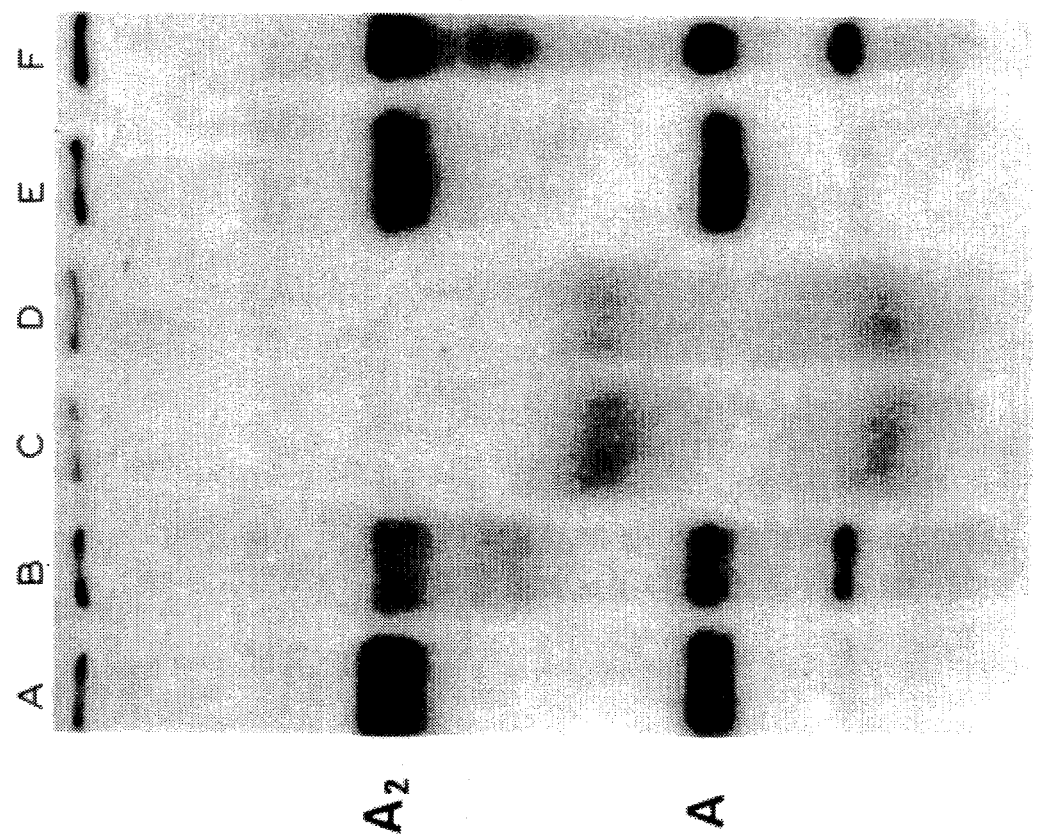

Protease purification:

Culture supernatants from a majority of the serotypes of *P. haemolytica* A1 contain a neutral protease (Otulaklowski, G. L. P. E. Shewen, A. E. Udoh, A. Mellors, and B. N. Wilkie. 1983. Proteolysis of Sialoglycoprotein by *Pasteurella Haemolytica* Cytotoxin Culture Supernatant. *Infect. Immun.* 42:64–70. FIG. 9 (A) shows that the culture supernatant from *P. haemolytica* A1 biotype A, serotype 1, contains an enzyme activity that cleaves human [$^{125}$I]-labelled glycophorin A, as revealed by the disappearance of dimeric glycophorin A and monomeric glycophorin A (lane a), to yield corresponding dimeric and monomeric products (lane b). Glycophorin A is the major sialoglycopeptide of the human erythrocyte membrane (Marchesi, V. T., H. Furthmayr, and M. Tomita. 1976. The Red Cell Membrane. *Ann. Rev. Biochem.* 45:667–698 and similar O-linked sialoglycopeptides are found on the cell surface of lymphoid cells (Fukuda, M., and S. R. Carlsson. 1986. Leukosialin, A Major Sialoglycoprotein on Human Leukocytes as Differentiation Antigens, *Med. Biol.* 64:335–343, Remold-O-Donnell, E., A. E. Davis III, D. Kenney, K. R. Bhaskar, and F. S. Rosen. 1986. Purification and Chemical Composition of gpL115, The Human Lymphocyte Surface Sialoglycophorin that is Defective in WiskottAldrich Syndrome. *J. Biol. Chem.* 261:7526–7530. When glycophorin A was extensively desialated by treatment with *Clostridium perfringens* neuraminidase, as monitored by Warren's assay (Warren, L. 1959. The Thiobarbituric acid assay of sialic acids. *J. Biol. Chem.* 234:1971–1975), little or no hydrolysis of the desialated dimeric or monomeric glycophorin, by the *P. haemolytica* protease, could be seen (lane d of FIG. 9(A)). The hydrolysis of glycophorin A can be inhibition by the presence of 100 mM EDTA, but this inhibition by high concentration of EDTA was removed by dialysis of the EDTA-inhibited enzyme (lane f FIG. 9(A)). FIG. 9(B) shows that if the incubation of the glycophorin A with *P. haemolytica* pH 4.5 fractions was prolonged, then total hydrolysis of the two forms of glycophorin A was observed.

To facilitate the purification of the enzyme, glycophorin was tritiated in situ in human erythrocyte ghost membranes by periodate oxidation and sodium-[$^3$H]-borohydride reduction. The [3H]-labelled erythrocyte ghosts were used to assay the enzyme activity during the purification of the proteolytic activity. Soluble radiolabelled glycophorin cannot be readily used in a simple enzyme assay, because neither the substrate nor the products can be precipitated. However, radiolabelled glycophorin in erythrocyte ghosts can be readily separated, by centrifugation, from the soluble radioactive glycopeptide products to thereby facilitate the assay.

The proteolytic activity of *P. haemolytica* A1 culture supernatants, against $^3$H-sialylated human erythrocyte ghosts, can be increased by dialysis of the supernatants, and by precipitation of an active protein fraction at pH 4.5 (Table 1). The increased specific activity is due partly to the removal of dialyzable inhibitors, and in part to the removal of inactive proteins in the pH 4.5 supernatant. The previously referred to leukotoxin of *P. haemolytica* A1 remains entirely in the supernatant while the protease is quantitatively precipitated. A seventeen-fold increase in the specific activity of the protease, and the removal of leukotoxin, is achieved in the pH 4.5 precipitation step. This precipitate can be readily redissolved in 0.05M HEPES buffer pH 7.4 and can be used in further studies for characterizing properties of the protease because of the its high stability compared with fractions that have lower protein concentrations.

Purification of the glycoprotease from serum-free culture supernatant was achieved by size-exclusion and ion-exchange column chromatography as shown in Table 2. Separation of the neuraminidase and protease activities was obtained when serum-free culture supernatants of *P. haemolytica* were concentrated by Amicon ultrafiltration and chromatographed by HPLC on TSK gel-exclusion colum. FIG. 10 shows that the neuraminidase is eluted in the void volume, but the glycophorin-degrading protease eluted mainly in a smaller M fraction. This protease-enriched fraction was chromatographed by HPLC on a MonoQ anion exchange column, and the protease eluted with the major protein peak (FIG. 11). The highest specific activity of the protease in a major fraction was 94 nmol per mg/h for glycophorin degradation, which was a 188-fold increase over the activity of the serum-free culture-supernatant, and recovery of the enzyme activity in this fraction was 80%. SDS-PAGE analysis of this fraction showed a major band at about 35,000 $M_T$ and this fraction cleaved glycophorin A (FIG. 11 inset). The isolation of a relatively homogeneous protein fraction with a glycoprotease activity similar to that found in the culture supernatant, suggests that the activity is a discrete enzyme and that multiple factors are not involved in the hydrolysis of glycophorin. No proteolysis was observed for chromatographic fractions other that those containing the 35 kD protein. However, protease activity was very unstable in fractions prepared from serum-free culture supernatants, compared with fractions containing serum proteins. Therefore, the stable activity of pH 4.5-precipitated extracts are preferred as protease isolates for the enzyme.

Substrate specificity:

Glycophorin A is a 31 kD human erythrocyte membrane glycoprotein and cannot be the physiological substrate for the *P. haemolytica* A1 protease.

However, few glycoproteins from bovine target cells are characterized and available for testing as potential in vivo substrates. When N-linked glycoproteins (immunoglobulins A1 and A2; bovine α-1 acid glycoprotein; bovine β-lactalbumin; and hen ovalbumin) were radiolabelled with $^{125}$I-iodine and incubated with partially-purified enzyme extracts (pH) 4.5-precipitated extract), no hydrolysis of these substrates could be detected, SDS-PAGE and autoradiography. The lack of hydrolysis for human immunoglobulin A1 (IgA1) or human immunoglobulin A2 (IgA2), means that the glcyophorindegrading enzyme is not identical to IgA protease, a microbial neutral metallo-protease (Labib, R. S., N. J. Calvanico, and T. B. Tomasi Jr. 1978. Studies on Extracellular Proteases of *Streptococcus sanguis*, Purification and Characterization of a Human IgA1 Specific Protease. *Biochem. Biophys. Acta.* 526:547–559, Plaut, A. G. 1983. The IgA1 Proteases of Pathogenic Bacteria. *Ann. Rev. Microbiol.* 37:603–622). A wide range of non-glycosylated proteins have been tested and found not be cleaved by the *P. haemolytica* A1 protease. The [$^{125}$I]-labelled proteins, bovine serum albumin, rabbit muscle glyceraldehyde-3-phosphate dehydrogenase, soybean trypsin inhibitor, bovine carbonic anhydrase, bovine trypsinogen and bovine chymotrypsinogen were not hydrolyzed by the protease. Other proteins were tested as substrates by incubation with active enzyme fractions, and enzyme action was monitored by SDS-PAGE and Coomassie blue staining of the substrate and products. The enzyme did not hydrolyze bovine insulin chain A, insulin chain B, or cytochrome c. Partially purified enzyme preparations with high activity against glycophorin were inactive in cleavage of dye-casein conjugates (Azocasein) or dye-collagen conjugates (Azocoll). Thus the weak casein-degrading activity reported in culture supernatants of *P. haemolytica* A1 (Otulakowski et al supra) was not found in the protease-enriched extracts used here. A number of small synthetic peptides, including substrates cleaved by bacterial serine proteases, thiol proteases and neutral metallo-proteases, have been tested as substrates for the *P. haemolytica* A1 protease but no hydrolysis of small peptides was observed. No inhibition of glycoprotease could be detected in the presence of conventional inhibitors of serine proteases (phenylmethanesulfonyl-fluoride or di-isopropylphosphofluoridate); thiol proteases (N-ethylmaleimide, p-chloromercuribenzoate or p-hydroxymercuribenzoate); chymotrypsin inhibitor (tosylphenylalanyl chloromethylketone) or trypsin inhibitor (tosyl-lysl chloromethylketone).

Properties of the protease:

The protease activity was stable at pH 7.0–7.5, but was destroyed rapidly above pH 8.0. The protease is inhibited by prolonged treatment (24 h) with 1,10-phenanthroline, so that it has been classified as a neutral metallo-protease. Table 3 shows that the hydrolysis of [$^{125}$I]-glycophorin is inhibited completely by 1 mM EDTA, in serum-free preparations of the enzyme, though more EDTA must be used to inhibit the enzyme if serum proteins are present, as for the pH 4.5 preparation (FIG. 9, lane e). However, dialysis against de-ionized (Milli-Q treated) distilled water to remove EDTA resulted in the reactivation of the enzyme, so that any metal ion activator must be tightly bound to the enzyme and not readily removed by EDTA (FIG. 9, lane f). The EDTA-inhibited *P. haemolytica* A1 protease activity could not be reactivated by the addition of metal ions. In assays not shown here, the addition of the divalent metal ions, $Zn^{2+}$, $Fe^{2+}$, $Mg^{2+}$ or $Ca^{2+}$ failed to restore the protease activity after EDTA treatment and dialysis of the enzyme, and failed to increase activity in the native enzyme. The anions citrate and ascorbate gave similar inhibitions of the serum-free enzyme to that given by EDTA. The inhibition probably arises from masking by the anions of tightly-bound metal ion activator on the enzyme, perhaps at some site which binds the anionic sialoglycoprotein substrates. A putative zinc-binding site can be seen in the primary sequence of the enzyme as predicted from the nucleotide sequence of the gene of FIG. 4 (SEQ ID NO:1). Free sealate did not inhibit the action of the glycoprotease liable 3). Phosphoramidon [N-(β-L-rhamnopyranosyl-oxyhydroxyphosphinyl)-L-leucyl-L-tryptophan] is a protein inhibitor of neutral metallo-proteases such as thermolysis, a protease of broad specificity (Malfroy, B., and J.-C.Schwartz. 1985. Comparison of Dipeptidyl Carboxypeptidase and Endopeptidase Activities in the Three Enkiphalin-hydrolysing Metallopeptidases: "angiotensin-converting enzyme, thermolysin, and "enkephalinase". *Biochem. Biophys. Res. Commun.* 130:372–378, but without significant effect on the *P. haemolytica* protease. Lack of inhibition by phosphoramidon is consistence with the inability of the enzyme to hydrolyze the thermolysin substrate, furoylacryloylglycylleucinamide (Otulakowski et al supra). The protease is not as heat-stable as is thermolysin. A 30 min preincubation of the enzyme at 40° C. gave rise to 38% loss of activity in the presence of 25 mM NaCl, and to 80% loss of activity in the absence of 25 mM NaCl. Unlike thermolysin, the enzyme was entirely inactivated by 30 min pre-incubation at 60° C., in the presence or absence of 25 mM NaCl.

Products of protease action on glycophorin:

The characterization of the products of protease action on glycophorin A, is technically difficult because the substrate and some products are over 60% carbohydrate, therefore these are highly soluble even in the presence of protein denaturants, and they exhibit anomalous electrophoretic behaviour (Futhmayr, H. 1978. Structural Comparison of Glycophorins and Immunochemical Analysis of Genetic Variants. *Nature* (London) 271:519–524. The amphipathic nature of glcyophorin, a membrane protein, means that the molecule is very susceptible to aggregation, even in the presence of detergents such as SDS (Segrest, J. P., I. Kahane, R. L. Jackson and V. T. Marchesi. 1973. Major Glycoprotein of the Human Erythrocyte Membrane: evidence for an amphipathic molecular structure. *Arch. Biochem. Biophys.* 155:167–183). A dimeric substrate, cleaved at one site, will give rise to more than two fragments. Glycoproteins are also known to exhibit anomalous effects such as aggregation and poor SDS-binding which affect their apparent $M_r$ values in chromatography and electrophoresis. Numerous attempts to sequence the major products, isolated by gel-exclusion chromatography or SDS-PAGE were frustrated by apparent N-terminal blockage or loss of the product in the first cycle of the Edman sequencing procedure. The sites of cleavage of glycophorin A by the glycoprotease were identified by immobilizing the enzyme onto nitrocellulose paper, with retention of enzyme activity. Glycophorin A was incubated with the immobilized enzyme for 3 h and for 18 h, and the products were identified by appearance of new N-terminal sequences, corresponding to internal sequences of the substrate (Table 4). The first major product arises by the cleavage of the peptide bond at Arg31-Asp32 in glycophorin A, but further hydrolysis occurs at other peptide bonds including Glu60-Arg61, Ala65-His66 and Tyr34-Ala35. The major cleavage sites are not due to contaminating proteases, since a similar pattern of product formation is seen for homogeneous preparations of the enzyme on prolonged incubation with radio-iodinated glycophorin A. No N-terminal exopeptidase activity was seen for the data of Table 4, as shown by the recovery of intact glycophorin N-terminal sequences. We have previously shown that the glycoprotease is not inhibited by a variety of trypsin and chymotrypsin inhibitors (Otulakowski et al. supra). Furthermore, the major cleavages of glycophorin A by trypsin and chymotrypsin are at Lys18 and Tyr20 respectively, which is different from the major site of cleavage of the glycoprotease between Arg31-Asp32. (Tomita, M., H. Furthmayr and V. T. Marchesi. 1978. Primary Structure of Human Erythrocyte Glycophorin A. Isolation and Characterization of peptides and Complete Amino Acid Sequence. *Biochemistry* 17:4756–4770, Tomita, M., and V. T. Marchesi. 1975. Amino Acid Sequence and Oligosaccharide Attachment Sites of Human Erythrocyte Glycophorin. *Proc. Natl. Acad. Sci. USA* 72:2964–2968).

In order to understand the use of the glycoprotease and the discovered DNA sequence, the following discussion identifies certain general areas of interest in the consequent use of the glycoprotease.

CD34 antibodies recognize primitive haematopoietic stem cells and their leukaemic counterparts.

Four monoclonal antibodies MY10 Civin et al. 1984, *J. Immunol*, B1.3C5 Katz et al. 1985. *Leuk.Res.*, 12.8 Andrews et al. 1986. *Blood* and ICH3 Watt et al. 1987. *Leukaemia* raised against KG1 or KG1a cells have been shown to identify an antigen on a small population of bone marrow cells. This subpopulation is shown by colony-forming assays to include virtually all unipotent (BFU-E, CFU-GM, CFU-Meg) and multipotent (CFU-GEMM and pre-CFU) progenitors Civin et al. 1984, *J. Immunol.*; Katz et al. 1985. *Leuk.Res.* MY10 has also been shown to bind to blast colony-forming cells in cord blood Strauss et al. 1986. *Exp. Hematol.* While mature lymphoid colony forming cells do not express the CD34 antigen, putative B lymphoid cell precursors with nuclear terminal deoxynucleotidyl transferase activity also react with B1.3C5 and MY10 Katz et al. 1985. *Leuk.Res.*; Strauss et al. 1986. *Exp. Hematol.*; Katz et al. 1986. *Exp. Hematol.* These and other studies, using fresh leukaemia samples, indicate that the CD34-positive progenitor cells of normal marrow contain precursors of myeloid cells Civin et al. 1984. *J. Immunol.*; Katz et al. 1985. *Leuk. Res.*; Andrews et al. 1986. *Blood*; Strauss et al. 1986. *Exp. Hematol.*; Katz et al. 1986. *Leukocyte Typing II, Oxford Univ. Press* and B cells Katz et al. 1985. *Leuk. Res.*; Katz et al. 1986. *Leucocyte Typing II, Oxford Univ. Press*; Ryan et al. 1986. *Blood*; Ryan et al. 1987. *Blood*. Recent analyses of rare T cell-ALLs with primitive T-cell characteristics Watt et al. 1987. *Leukaemia*; Schuh et al. 1987. *Blood* and the undifferentiated T-cell leukaemia-derived cell lines Molt-13 Watt et al. 1987. *Leukaemia* and RPM1 8402 Fackler et al. 1990. *J. Biol. Chem.*, strongly suggest that mature blood cells of all lineages are derived from the CD34-positive fraction of normal marrow. This is supported by the observation that CD34-positive bone marrow cells can reconstitute all lineages of the haematopoietic system in lethally-irradiated baboons. Animals receiving the CD34-negative fraction, failed to engraft Berenson et al. 1988. *J. Biol. Chem.* A preliminary report of the transplant of CD34-positive cells in 3 women with metastatic breast cancer supports the view that isolated CD34-positive marrow cells are also capable of reconstituting haematopoiesis in humans Berenson et al. 1988. *Exp. Hematol.* Recent single-cell cloning experiments demonstrate that highly purified CD34-positive cells, which lack co-expression of all myeloid T- or B-cell antigens, are capable of generating several types of colonies when grown over irradiated stromal cells in vitro Andrews et al. 1990, *J. Exp. Med.*

In healthy individuals, CD34 expression is confined to pan-haematopoietic cells in the bone marrow, with the exception of capillary endothelial cells, which are CD34-positive on immunohistologic staining Watt et al. 1987. *Leukaemia*; Beschomer et al. 1985. *Am. j. Path.*; Sutherland et al. 1986. *Blood*; Fina et al. 1990. *Blood*. Tumour expression of CD34 tends to mirror normal expression. Essentially all non-haematologic tumours are unreactive Watt et al. 1987. *Leukaemia*. About 40% of AMLs (mainly FAB M1 class) and 65% of cells are reactive Katz et al. 1986 *Leucocyte Typing II, Oxford Univ. Press* whereas only 1–5% of acute T-lymphoid leukaemia are reactive Civin et al. 1989. *Leucocyte Typing IV, Oxford Univ. Press*. Chronic leukaemia and lymphomas of more differentiated phenotype are uniformly negative Katz et al. 1986. *Leukocyte Typing II, Oxford Univ. Press*; Civin et al. 1989. *Leukocyte Typing IV, Oxford Univ. Press*

CD34 is a highly glycosylated 110 kD molecule in leukaemic cells.

All CD34 antibodies recently assessed for the International Workshop on Leucocyte Differentiation Antigens, immunoprecipitate a monomeric structure of 110 kD from lysates of acute myelogenous leukaemia-derived cell lines KG1 and KG1a Civin et al. 1984. *J. Immunol.*; Katz et al. 1985. *Leuk. Res.*; Andrews et al. 1986. *Blood*; Watt et al. 1987. *Leukaemia*. Similar bands can be isolated from fresh acute leukaemia of primitive myeloid, B-lymphoid and T-lymphoid phenotypes Katz et al. 1985. *Leuk. Res.*; Schuh et al. 1990. *Leukaemia* (in press). Most CD34 antibodies identify denaturation-resistant epitopes in western blots, though with widely different efficiencies Civin et al. 1989. *Leucocyte Typing IV, Oxford Univ. Press*. These antibodies recognize a variety of distinct epitopes on this antigen, some of which MY10, B1.3C5, 12.8, we have shown to be dependent on the presence of sialic acid residues. Extensive structural and carbohydrate analyses indicated the presence of O-linked glycans Fina et al. 1990. *Blood*; Sutherland et al. 1988. *Leukaemia*. Partial aminoacid sequence analysis has revealed no similarities with previously-described structures Sutherland et al. 1988. *Leukaemia*. The CD34 cDNA has recently been cloned using a mammalian expression system, COS-7 cells. It predicts that CD34 is a type I integral membrane protein of 40 kD, with 9 potential N-glycosylation sites. Since the de-N-glycosylated and desialylated forms are 90 kD and 150 kD respectively Sutherland et al. 1988. *Leukaemia*, the native molecule must contain a considerable number of O-linked glycans. Accordingly over 35% of the amino acids in the N-terminal domain probably ensure that it takes on the conformation of and extended rigid "pole". Thus the $NH_2$-terminus of the CD34 antigen can be expected to extend a considerable distance out from the cell membrane.

CD34 is a substrate for the *P. haemolytica* glycoprotease.

The progenitor-cell-restricted antigen CD34 on KG1 cells is readily cleaved by the *P. haemolytica* glycoprotease as shown by the loss of reactivity of this antigen with the anti-CD34 monoclonal antibody B1.3C5 Sutherland et al. 1990. *Blood*; Katz et al. 1985. *Leuk. Res.* which detects a sialic acid-dependent epitope on this glycoprotein Watt et al. 1987. *Leukaemia*; and Sutherland et al. 1988. *Leukaemia*. We have assessed the ability of this enzyme to remove CD34 epitopes recognized by all seven CD34 antibodies designated by the 4th Leucocyte Antigen Workshop Civin et al. 1989. *Leukocyte Typing IV, Oxford Univ. Press*. We have shown by fluorescence microscopy, quantitative flow cytometry and western blotting, that sialic acid-dependent epitopes, recognized by antibodies B1.3C5, MY10 Civin et al. 1984. *J. Immunol.* and 12.8 Andrews et la. 1986. *Blood*, are totally removed,as are the sialic acid-independent epitopes recognized by ICH3 Watt et al. 1987. *Leukaemia* and 188.24 Sutherland et al. *Leukaemia*. In contrast, the sialic acid-independent epitopes by 115.2 Andrew et al. 1986. *Blood* and TUK3 Civin et al. 1989. *Leucocyte Typing IV, Oxford Univ. Press* are totally resistant to the action of the glycoprotease. As previously for the cleavage of glycophorin, the enzyme requires the presence of sialyted residues on its substrate and the prior treatment of KGla cells with neuraminidase reduced the ability of the glycoprotease to cleave the ICH3 and 188.24 epitopes Sutherland et al. 1990. *Blood* (in press). The differential sensitivity of certain CD34 epitopes to cleavage with either neuraminidase and/or glycoprotease establishes 3 classes of epitopes:(Class 1) those like MY 10,B1.3C5 and 12.8 which are removed both by neuraminidase and by the glycoprotease;(Class II) those like ICH3 and 188.24 which are removed only by the glycoprotease; (Class III) those like TUK3 and 115.2 which are removed by either enzyme. Polyclonal rabbit antibody will be raised against the *P. haemolytica* glycoprotease by injecting the pure enzyme expressed as the product of the recombinant gene.

For the study of the properties of the *P. haemolytica* glycoprotease, the enzyme used is the recombinant product in *E. coli* HB101 of the gene gpc, in the high-expression vector pTTQ18. The recombinant gene product is secreted into the periplasmic space of the host and has the advantage of being free from *P. haemolytica* proteins and most host proteins. The periplasmic enzyme free from host proteins is isolated by osmotic-shock, followed by SDS-PAGE analysis. The enzyme band is clearly visible at 35 kD by Coomassie staining and is cut from the gel and injected s.c. into rabbits. Rabbit sera is tested for specific antibody by western blotting against culture supernatant enzyme, with controls for host cell *E. coli* lysates. These antibodies are used to make an immuno-affinity column by crosslinking them to Protein A-Sepharose Schneider et al. 1982. *J. Biol. Chem.* The affinity column is used for the rapid isolation of the enzyme, both from the recombinant *E. coli* and from culture supernatants of *P. haemolytica*. The enzyme can be eluted from the affinity-column under conditions which give maximum recovery of active enzyme, as assessed by the hydrolysis of radio-iodinated glycophorin A. The homogeneous native glycoprotease can be used to raise a series of monoclonal antibodies which can modulate the enzyme's activity. Neutralizing antibodies to the glycoprotease are needed to determine specific actions of the enzyme in altering the structures and functions of cell-surface antigens.

Four cell-surface O-sialoglycoproteins, of known aminoacid sequence, are cleaved by the enzyme, and the products of cleavage isolated and characterized.

In our previous work, we have concentrated on the cleavage of human erythrocyte glycophorin A by the *P. haemolytica glycoprotease* Udoh et al. 1986. *Univ. of Guelph*; Abdullah et al. 1988. *Proc. Canad. Fed. Biol. Socs.*; Abdullah et al. 1990. *Biochem. Soc. Trans*. This substrate is well-characterized erythrocyte surface O-sialoglycoprotein and is readily available for biochemical analysis. However, it is clear that the physiological targets of this enzyme are not erthrocyte antigens but are probably O-sialoglycoproteins on the surfaces of leukocytes or endothelial cells. SDS-PAGE analysis of immunoprecipitations performed with specific monoclonal antibodies on lysates of surface-$^{125}$I-iodinated KG1a cells, a primitive myeloid/T-lymphois stem cell line Koeffler et al. 1977. *Science* 200, have shown that the O-sialoglycoprotein cell surface antigens CD34 Civin et al. 1989. *Leucocyte Typing IV, Oxford Univ. Press*. CD43/leucosialin Killeen et al. 1987. *EMBO J.*; Pallant et al. 1989. PNAS, CD44/lyaluronic acid receptor Stamenkovic et al. 1989. Cell; Aruffo et al. 1990. *Cell* and CD45/leucocyte common antigen Thomas et al. 1989. *Annu. REv. Immunol.*; Pulido et al. 1989. *J. Immunol.* are all cleaved by the glycoprotease. Although the glycoprotease-sensitive structures contain some N-linked glycans they are all extensively glycosylated with O-linked carbohydrates. However, the N-linked glycoproteins CD18/11$^a$, 11$^b$, 11$^c$/leukocyte integrins Arnaout et al. 1990. *Blood*, CD71/transferrin receptor Shae et al. 1986. *Cell*, HLA class I Owen et al. 1980. *J. Biol. Chem.*, and 8A3 antigens Sutherland et al. *Blood* (in press, Jan. 1991), which lack O-sialo-residues, were resistant to the action of the enzyme.

O-sialoglycoproteins on cell surfaces have been implicated in a number of roles in normal cells, and aberrant glycosylation has been detected in a number of tumours Kanani et al. 1990. *Can. Res.* To confirm the utility of this enzyme in the analysis of glycoprotein structure and function of cell structure antigens, the list of susceptible cell-surfaces can be readily extended. There are other blood cell O-sialoglycoproteins which would be substrates for the glycoprotease, including the T-cell associated antigens CD7 Sutherland et al. 1984. *J. Immunol.* and CD25/IL-2-receptor α chain Leonard et al. 1983. *J. Immunol.*; the pre-B cell associated antigens CD9 Newman et al. 1982. *Biochim. Biophs.* Acta and CD24 Pirucello et al. 1986. *J. Immunol.*, and the platelet/endothelial cell antigen, thrombomodulin Dirtman et al. 1990. *Blood.* The latter glycoprotein is an endogenous anticoagulant, and has potential uses in the control of cancer coagulopathies. Thrombomodulin bears some structural resemblance, in its domain organization, to another membrane O-sialoglycoprotein, the low density lipoprotein (LDL) receptor Russell et al. 1983. *Cell.*

To confirm that the enzyme is specific for O-linked glycoproteins, other N-linked antigens can be tested as controls, including CD13 on KG1 and CD10 on pre-B cell lines.

The products of cleavage of the four O-sialoglycoprotein substrates are analyzed by N-terminal sequencing, so that the susceptible peptide bonds can be identified.

The sites of cleavage of glycophorin A have shown that the glycoprotease is unique. Its restricted substrate specificity for O-sialoglycoproteins is shared by no other enzyme. The enzyme does not show the characteristic inhibitor or activator sensitivities of other known protease classes, for example, the serine proteases, thiol proteases, aspartate proteases or neutral metalloproteases Abdullah et al. 1988. *Proc. Canad. Fed. Biol. Socs*. The primary structure of the glycoprotease, predicted from the nucleotide sequence of the gene, shows no homology with other proteases of procaryotic or eucaryotic origin. The peptide bond specificity of the glycoprotease as further defined, permits study of structure-function relationships in substrate glycoproteins and cell-surface antigens. For example, we can use five O-sialoglycoprotein antigens, glycophorin A, CD34, CD44, CD45 and thrombomodulin, whose amino-acid sequences are known Tomita et al. 1975. *PNAS*; Sutherland et al. 1988. *Leukaemia*; Stamenkovic et al. 1989. *Cell*; Jackman et al. 1986. *PNAS*, and which are readily available. We have shown that the first four antigens in this list are cleaved by the enzyme. Hydrolysis of glycophorin A can be carried out by the glycoprotease immobilized on nitrocellulose, which retains its activity and generates soluble products. The products can be isolated by SDS-PAGE under conditions which prevent blockage of the new N-terminal sequences Moos et al. 1989. *J. Biol. Chem.* and electrophoretically blotted onto PVDF membranes (Immobilon) for N-terminal sequencing on a gas-phase microsequencer.

The analysis of the sites of glycoprotease cleavage of CD34 and CD44 were performed on soluble CD34:IgG and CD44:IgG fusion proteins, chimeric molecules comprising the extracellular domains of either CD34 or CD44 ligated to the Fc' domain of the human $IgG_1$ molecule. The fusion proteins are secreted into the medium to concentrations of 0.5 µg/ml by COS-7 cells transfected with the appropriated genetically-engineered plasmid Seed et al. 1987. *PNAS* and can be rapidly isolated from the medium by Protein A-Sepharose affinity chromatography. Purity is assessed by SDS-PAGE and silver staining. The purified CD34:IgG fusion protein is analyzed by SDS-PAGE and western blots, with three sialate-dependent CD34 antibodies MY10, B1.3C5 and 12.8 (supra). Duplicate blots are neuraminidase-treated before additions of the antibodies. The fusion protein is cleaved with the *P. haemolytica* glycoprotease and the products are chromatographed on Protein A-Sepharose affinity columns, to remove N-terminal fragments. The bound material is eluted and an aliquot analyzed by SDS-PAGE and silver staining.

The approach described above for the determination of the site(s) of cleavage of CD34, was also used to analyze the other cleavage product for the CD44 molecule. Our experiments indicate that the 85kD cell-surface CD44 molecule is split by the glycoprotease to yield two new bands of about 40 kD and 50 kD, and suggest that there are two equally-susceptible sites of cleavage in the CD44 molecule.

The use of glycoprotease to test the involvement of specific sialoglycoprotein antigens in transmembrane signalling during immune cell response.

As described above, the *P. haemolytica* glycoprotease can cleave a number of O-sialoglycoproteins in the glycocalyx of living cells. The enzyme does not show any cellular toxicity and does not cleave other proteins and N-glycosylated proteins on the cell surface. Therefore, the enzyme can be a powerful new reagent with which to test current theories on the roles of O-sialoglycoproteins Jentoft et al. 1990. *Trends in Biochem. Sci.* It has been suggested that the primary purpose of O-glycosylation on the cell surface is to limit access to the plasma membrane by bacteria, viruses, toxins and cells of the immune system. A second general role for O-glycosylation may be the reduction of proteolysis and turnover for proteins which bear O-sialoglycosyl residues Kozarski et al. 1988. *PNAS*. In both cases, the high density of negative charge conferred by sialate would inhibit the approach of other negatively charged residues on other cells or enzymes. However, no matter what general effects may be attributed to the bulk of the O-glycoproteins on cell surfaces, there are indications of specialized biochemical roles for some cell surface O-glycoproteins. For example, CD43/leucosialin has been implicated in transmembrane signalling Wong et al. 1990. *J. Immunol.* and the adhesion molecule, CD44, has been identified as hyaluronate receptor on the cell surface Aruffo et al. 1990. *Cell*. The leukocyte common antigen, CD45, has an extracellular domain, thought to be involved in ligand binding, and an intracellular domain with protein phosphotyrosine phosphatase activity, so that it too may be a transmembrane signalling molecule, Thomas et al. 1989. *Annu. Rev. Immunol*. Other cell-surface O-sialoglycoproteins with defined functions include the aforementioned LDL-receptor, the IL2-receptor-α-subunit CD25 and thrombomodulin. Since the action of the *P. haemolytica* glycoprotease appears to be restricted to this class of molecules, the enzyme can be used to confirm specific functions for known O-glycoproteins. The enzyme can also be use to diagnose the involvement of unknown O-sialogycoproteins in cellular response.

The role of cell surface O-sialoglycoproteins as cell adhesion molecules can be tested by cleaving these with the *P. haemolytica* glycoprotease and measuring the ability of the products to bind to specific ligands.

The CD44 antigen has been implicated in the specific homing of leucocytes to specialized areas of endothelial cells which line the post-capillary venules (High Endothelial Venule cells). Some monoclonal antibodies to this structure can specifically block this adhesion to HEVs Jalkanen et al. 1988. *J. Immunol.* The recent cloning of the cDNA for CD44 confirmed the presence of N-linked and O-linked glycans and also revealed the presence of four potential chondroitin sulfate linkage sites Stamenkovic et al. 1989. *Cell*. Sequence homology between CD44 and the proteoglycan-link proteins suggested that CD44 may function as an extracellular matrix-binding adhesion molecule. This is supported by the recent finding that CD44 can bind with high affinity to hyaluronic acid, a component of the extracellular matrix Aruffo et al. 1990. *Cell*. The CD44:IgG chimeric protein can be cleaved with *P. haemolytica* glycoprotease and thereby assess the ability of the cleaved CD44:IgG to bind to hyaluronic acid. CD44 has also been shown to bind to other components of the extracellular matrix, chondroitin-4-sulfate and chondroitin-6-sulfate, though with much lower affinity than that for hyaluronate Aruffo et al. 1990. *Cell*. We can now assess the ability of the cleaved CD44:IgG molecule to bind to these chondroitin sulfates.

The roles of O-sialoglycoproteins in cell activation can be tested in responding cells from which cell surface molecules have been cleaved by the *P. haemolytica* glycoprotease.

CD43/leucosialin is an O-sialoglycoprotein expressed in a variety of glycosylated forms on human leucocytes. While its function is unknown, defective expression of the molecule has been associated with an immunodeficiency disease, the Wiskott-Aldrich syndrome Parkman et al. 1981. *Lancet* 2; Greet et al. 1989. *Biochem. Cell. Biol.* Monoclonal antibodies against CD43 induce monocytedependent T-cell proliferation, and stimulation adhesion and hydrogen peroxide production in monocytes. Activation of T cells via anti-CD43 antibodies is associated with increases in intracellular $Ca^{2+}$, inositol phosphates and diacylglycerol Wong et al. 1990. *J. Immunol.* We can now determine the effect of the glycoprotease on the intracellular increases in calcium induced by a rabbit anti-CD43 antibody (gift from M. Fukuda, La Jolla, Calif.) in human PBL cells, loaded with the acetoxymethyl ester of INDO-1, a fluorescent indicator of $[Ca^{2+}]_i$ Grynkiewicz et al. 1985. *J. Biol. Chem.*; Ebanks et al. 1989. *Biochem J.*

The progression of activated cells through the cell cycle as a result of stimulation by lymphokines, will be tested in cells which have been treated with the *P. haemolytica* glycoprotease to remove cell surface O-sialoglycoproteins.

T-cells can be stimulated to proliferate by mitogens and growth factors that are thought to act via O-sialoglycoprotein receptors or receptor complexes on the T-cell surface. We have used the murine T cell line LBRM 331A which secretes IL-2 in response to mitogens, such as PHA, in the presence of the lymphokine IL-1 and phorbol ester (TPA) Mills et al. 1990. *J. Cell. Physiol.* Treatment of these cells with the *P. haemolytica* glycoprotease concomitant with stimulation with mitogens for four hours gave enhanced IL-2 secretion in the treated cells compared to controls. The glycoprotease preparation was not significantly mitogenic of itself, and was non-toxic to the treated cells. The data suggest that PHA and IL-1 do not stimulate cells via receptors that have O-sialoglycoproteins structures that are susceptible to hydrolysis by the enzyme under these conditions The removal of O-sialoglycoproteins from T cell surfaces may enhance the production of IL-2 in response to extracellular mitogens or Il-1. There may be increased binding of ligands to receptors, due to the removal of some negatively charged glycopeptides on the cell surface.

The murine T cell line CTLL-2 proliferates in response to IL-2 and was used to test the effect of the glycoprotease on IL-2 sensitivity. The IL2-receptor x-subunit (CD25) is an O-sialoglycoprotein and may be susceptible to the enzyme, as measured by proliferation, over a wide range of IL-2 concentrations. Enzyme treatment alone was not mitogenic for the CTLL-2 cells. By the use of mouse monoclonal antibodies anti-TAC and 7G7.B6, which recognize different epitopes on the human IL-2R x chain, visualized by fluorescence microscopy using FITC-goat-anti-mouce Ig, we can determine whether the enzyme treatment leads to any change in the surface expression of the receptor. The enhanced sensitivity of the CTLL-2 cells to IL-2 may be due to unmasking of receptors by the removal of other O-glycoproteins of the glycocalyx. In control experiments the cell surface expression of another component of the IL-2 receptor, the Il-2-R β-subunit, can be monitored using the antibody DU2. This polyclonal antibody recognizes an extracellular domain and reveal any unmasking of the receptor that is induced by enzyme treatment.

We can use the pre-B cell line BAF3-F7 to determine the effect of the enzyme on Il-2 and IL-3 receptors. This mouse cell line constitutively expresses the Il-2R α-subunit and has been transfected with the gene for the human Il-2R β-subunit, so that it will proliferate in the presence of Il-2, and it can be stimulated by IL-3. Thus we can compare the enzyme effects on two lymphokine receptors in the same cell. We have seen increases in sensitivities to both Il-2 and to IL-3 in these cells after treatment with the glycoprotease, with the more marked increases being seen for IL-3 induced proliferation.

Some cell surface O-sialoglycoproteins are thought to be involved in cell-cell interactions, and these interactions can be modified by cleaving such surface antigens with the glycoprotease enzyme. We can test the effect of the enzyme on the in vitro MLR (mixed leucocyte reaction), in which human peripheral blood leucocytes (PBL) from one donor are irradiated and mixed with the non-irradiated PBLs of a second donor. The resultant cell-mediated proliferation over 72 h is monitored by $^3$H-thymidine incorporation. Enzyme-treated irradiated cells can be used with normal responder cells, and normal irradiated cell can be used with enzyme-treated responder cells. Glycoprotease treatment will be for 30–60 min, and cells will be washed before mixing. Proliferation can be measured for all combinations of treated and untreated cells. The MLR experiments should reveal whether the responder cells or the antigen-bearing irradiated cells are sensitive to glycoprotease treatment.

The natural anticoagulant factor, thrombomodulin, found on human platelet and endothelial cells, will be solubilized by cleavage with *P. haemolytica* glycoprotease and soluble products will be tested for their functionality in the clotting cascade.

Disseminated intravascular coagulopathy is a significant cause of mortality and morbidity in cancer patients Dvorak et al. 1986. *Human Pathol.* The excessive clotting observed in these patients is caused by an overproduction of thrombin, and is very difficult to treat Dvorak et al. 1987 "In Haematosis and Thrombosis" ed. Maden, Hirsch et al. Thrombomodulin is a potent inhibitor of the blood clotting cascade and is found on the surface of platelet and endothelial cells. It forms a 1:1 complex with thrombin, which converts Protein C to activated Protein C, which in turn cleaves other activated coagulation cofactors. Thrombomodulin is type 1 transmembrane glycoprotein, with a proximal extracellular region rich in serine and theonine, potential sites of 0-glycosylation. The domain organisation of thrombomodulin closely resembles that of the LDL-receptor Jackman et al. 1986. *PNAS.* Such organization is thought to be crucial for receptor mediated endocytosis and supports the hypothesis that the function of thrombomodulin is to aid the internalization of thrombin. Soluble forms of thrombomodulin may have potential therapeutic use in the treatment of coagulation disorders, such as DIC.

The following examples illustrate the cloning of the gene which encodes for the glycoprotease in the development of antibodies thereto. Such examples are not intended to be limiting in any way to the scope of the invention.

Material and Methods

Bacterial strains, plasmids and culture conditions:

*E. coli* strains HB101, TG-1, CSR603 and *P. haemolytica* A1 have been described previously Lo et al. 1986. "A simple immunological detection method for the direct screening of genes from clone banks." *Can. J. Biochem. & Cell Biol*; Lo et al. 1985. "Cloning and Expression of the Leukotoxin Gene of *Pasteurella haemolytica* A1 in *Escherichia coli* K-12." *Infect. Immun.*; Sancar et al. 1979. "A simple method for identification of plasmid-coded proteins." *J. Bacteriol.* The preparation of a clone bank which contains the *P. haemolytica* A1 genomic DNA carried in the vector pBR 322 has also been described Lo et al. 1985. "Cloning and Expression of the Leukotoxin Gene of *Pasteurella haemolytica* A1 in *Escherichia coli* K-12." *Infect. Immun.* The *E. coli* recombinant clones and in particular pPH1 and pPH8 which encode soluble antigens of *P. haemolytica* A1 were isolated using an antiserum directed against *P. haemolytica* soluble antigens in a colony immumoblot assay Lo et al. 1986. "A simple immunological detection method for the direct screening of genes from clone banks." *Biochem*. The M13 phage vectors mp18 and mp19 and the expression vectors pTTQ18 and pTTQ19 were from Pharmacia Chemicals Inc. (Dorval, QUE.). The *E. coli* HB101 clones were cultured in LT medium supplemented with ampicillin to 100 µg/ml (LT+A) Lo et al. 1986. "A simple immunological detection method for the direct screening of genes from clone banks." *Can. J. Biochem. & Cell Biol*. *P. haemolytica* cultures were grown in brain heart infusion broth (BHIB). *E. coli* TG-1 was grown on Davis minimal medium Miller, J. H. 1972. "Experiments in Molecular Genetics." Cold Spring Harbor Laboratory.

Enzymes and chemicals:

All restriction endonucleases and DNA-modifying enzymes were from Bethesda Research Labs. (Burlington, ONT) or Pharmacia Chemicals Inc. and were used as recommended by the supplier. Goat anti-rabbit immunoglobulin G-alkaline phosphatase conjugate, and colour development reagents, were purchased from Bio-Rad Labs. (Mississauga, ONT) or Sigma Chemicals (St. Louis, Mo.) [$\alpha^{32}$P] -dATP (3000 Ci/mmole) and Tran$^{35}$S-Label (1130 Ci/mmole) were from ICN Biochemicals (St. Laurent, QUE) and Immobilon™ polyvinylidene diflouride (PVDF) membranes were from Millipore (Mississauga, ONT).

EXAMPLE 1

Screening for glycoprotease activity and enzyme assay:

The *E. coli* recombinant clones were grown in LT+A broth overnight, subcultured (1/100) and grown for 4 h at 37° C. to logarithmic phase. The cells were harvested by centrifugation (5000×g), washed in 50 mM N-2-hydroxyethylpiperazine-N$^1$ -ethanesulfonic acid (HEPES) buffer (pH 7.4) and lysed by passing through a French press three times at a pressure of 17,000 psi. The lysates were centrifuged at 1,085×g for 5 min. to remove cellular debris and the supernatant, 0.1 ml was incubated with 5 µg $^{125}$I-glycophorin A (20 µCi/mg), prepared as described (10,11), in 0.1 ml 50 mM HEPES buffer (pH 7.4) for 16 h at 37° C. The unhydrolysed substrate and products of hydrolysis were separated by sodium dodecyl sulfate polyacrylamide gel electrophoresis (SDS-PAGE) Laemmli, U.K. 1970. "Cleavage of structural proteins during the assembly of the head of bacteriophage T4." *Nature* and detected by autoradiography using Cronex 4 X-ray film (Dupont, Wilmington DE). The enzyme activity of the glycoprotease was calculated from the percentage disappearance of glycophorin A bands as determined by slicing the gel and counting the band in a gamma counter.

EXAMPLE 2

In vivo labelling of cloned glycoprotease:

The recombinant plasmids which included pPH1 were transformed in *E. coli* CSR603 and maxi-cells were prepared Sancar et al. 1979. "A simple method for identification of plasmid-coded proteins." *J. Bacteriol*. *E. coli* CSR603 carrying the recombinant plasmids were grown to mid-logarithmic phase at 37° C. in Davis minimal medium supplemented with ampicillin and 0.5% caseamino acids. Then 10 ml of the culture was irradiated for 15 sec at 400 µW/cm$^2$ using a G-E germicidal lamp (General Electric). After culturing for 2 h, 100 µl D-cycloserine (2 mg/ml) was added and the culture was grown overnight. Approximately 3 ml of the culture was centrifuged and the washed pellet resuspended in 0.75 ml Davis minimal medium supplemented with theonine (10 mg/ml), argine (15 mg/ml), leucine (15 mg/ml) and proline (10 mg/ml). The cell suspension was incubated for 1 h at 37° C., after which 25 µCi of Tran $^{35}$S-Label was added. For recombinants in the expression vectors pTTQ18 or pTTQ19, isopropyl-β-D-thiogalactoside (IPTG, 0.5 mM) was included for induction of the tac promoter. After labelling for 1 h, the cells were harvested in a microfuge and lysed by resuspension in 150 µl of SDS-sample buffer Laemmli, U. K. 1970. "Cleavage of structural proteins during the assembly of the head of bacteriophage T4." *Nature*. The labelled proteins were separated by SDS-PAGE according to Laemmli, U. K. 1970. "Cleavage of structural proteins during the assembly of the head of bacteriophage T4." *Nature* and identified by direct autoradiography of the dried gel.

EXAMPLE 3

Subcloning and DNA sequencing:

The 3.3 kbp BamHI-BglII fragment of FIG. 2 from pPH1 was subcloned into the BamHI site of the expression vector pTTQ19. Selective fragments were removed from the insert DNA by digestion and religation with an endonuclease having a restriction site located on the insert DNA and one on the multicloning site in pTTQ19. A series of subclones were created each containing only selected fragments of the original insert DNA for pPH1. Each subclone was then analyzed for the expression of the glycoprotease in the *E. coli* maxi-cell system. A 2.3 kbp BamHI-HindIII fragment of FIG. 2 was determined to contain the glycoprotease gene. This fragment was subcloned into the M13 phage vectors mp18 and mp19 which propagated in *E. coli* TG-1. The nucleotide sequence of the insert DNA was determined by the dideoxy-chain termination method as described previously Dale, et al. 1985. "A rapid single-stranded cloning strategy for producing a sequential series of overlapping clones for use in DNA sequencing: application to sequencing the corn mitochondria 18s rDNA." *Plasmid*. The method of Dale was used to generate overlapping deletions of the insert DNA in either M13, mp18 or mp19 vectors for sequencing of the whole insert DNA. The DNA sequence was analyzed by using the Pustell Sequence Analysis program (IBI, Toronto, ONT). The nucleotide data base Genbank® was screened against the coding sequence, to search for sequence homology.

EXAMPLE 4

Expression of the glycoprotease (SEQ ID NO:1) gene:

The 2.3 kbp BamHI-HindIII fragment from pPH1 was subcloned into the expression vector pTTQ18 to form the plasmid pGP1. Expression was carried out by transformation of *E. coli* HB101 with pGP1. Cultures were grown overnight at 37° C. in LT+A broth. The cultures were then harvested by centrifugation (5,000×g) and the pellet was resuspended into prewarmed LT medium (without glucose) supplemented with ampicillin and IPTG (0.5 mM) and grown for 90 min at 37° C. The culture was centrifuged 5,000×g) and the pellet resuspended in 0.1 vol. of 2X sodium dodecyl sulfate (SDS)-sample buffer Lemmli, U. K. 1970. "Cleavage of structural proteins during the assembly of the head of bacteriophage T4". *Nature*. After boiling for 5 min the samples were separated by SDS-PAGE. The proteins were visualized by staining with Coomassie brilliant blue R250. For the determination of glycoprotease activity, the cells were lysed by French press and the lysate assayed for activity as described above.

EXAMPLE 5

Preparation of antiserum against glycoprotease.

The glycoprotease expressed from pGP1 was separated by preparative SDS-PAGE and stained with Coomassie brilliant blue R250. The gel fragment containing the glycoprotease was excised, homogenized in 1 ml saline containing the adjuvant saponin (Quil-A, Superfos a/s, Vedbek, Denmark) to yield an inoculum of 50 µg of Quil-A per rabbit. This was injected subcutaneously into two Pasteurella multocida-free New Zealand white rabbits (Hazelton Research Products Inc., Denver, Col.) at two week intervals. Serum was collected one week after the second injection and tested for glycoproteaseneutralizing activity. The serum used for Western-immuno blot analysis had titre of 1/100.

EXAMPLE 6

N-terminal amino acid analysis:

The glycoprotease expressed from pGP1 was recovered after SDS-PAGE and transferred by electroblotting onto PVDF membrane Walsh et al. 1988. "Extended N-terminal sequencing of proteins of Archaebacterial Ribosome blotted from two-dimensional gels onto glass fibre and PVDF membrane." *Biochemistry*. The PVDF membrane was stained with Coomassie blue R250, to located the gene product, destained and the appropriated region carrying the glycoprotease was sliced out. The glycoprotease was then subjected to N-terminal amino acid analysis by the automated Edman procedure in a gas-phase peptide microsequencer.

The following examples provide a preferred methodology for isolating the glycoprotease from culture of a selected suitable serotype of *P. haemolytica* and its purification.

In addition, examples are provided of further characteristics of the glycoprotease.

MATERIALS AND METHODS

Bacteria and culture conditions: *P. haemolytica* A1 (biotype A, serotype i was originally obtained from E. L. Biberstein, University of California, Davis, and is available under ATCC accession No. 43270. Stock organisms wer stored as lyophilized cultures after freeze-drying in distilled water containing 5% (w/v) destran, $M_T$ 70,000; 7% (w/v) sucrose and 1% (w/v) monosodium glutamate. Lyophilized *P. haemolytica* serotype 1 was inoculated into a blood agar plate and incubated at 37° C. for 16–18 h. A few colonies were inoculated into 250 ml of brain heart infusion broth (BHIB) and incubated with shaking at 37° C. for 4.5 h, the optimal time for enzyme production. The culture was centrifuged (8000×g) and the cells were resuspended into 500 mil of RPMI medium 1640 (Gibco Laboratories, Grand Island, N.Y.) containing 7% heat-inactivated fetal calf serum. For serum-free cultutre, only RPMI medium was used. The culture was grown for 3–4 h to midlog phase at 37° C. on a shaker, centrifuged (10,000×g) and the supernatant filter through a 0.2 µm Millipore filter. The filtrate was dialyzed against distilled water for 48 h at 4° C. and lyophilized.

Purification of the *P. haemolytica* A1 protease:

The lyophilized *P. haemolytica* A1 culture supernatant was dissolved in distilled water (30 mg/ml) and was acidified to pH 4.5, with 10.M acetate buffer pH 4.0, to give 6 mM acetate concentration. After 30 min at 4° C., the precipitate which formed was removed by centrifuagation at 47,000×g for 10 min. The precipitate contained most of the proteolytic activity and the supernatant contained all the leukotoxin activity. The precipitate was dissolved at 400 mg of lyophilized material per ml in 0.05M HEPES (4-(2-hydroxyethyl)-1-piperazine-ethane sulfonate) buffer, pH 7.4, for some enzyme assays, and is referred to as the pH 4.5 fraction. Isolation of a homogeneous glycoprotease activity was achieved by HPLC separation of a serum-free culture supernatant preparation. Serum-free culture supernatant of *P. haemolytica* was concentrated by Amicon PM-10 membrane ultrafiltration to yield 0.5 mg/ml protein and 100 µg of this protein was separated by gel-permeation HPLC, on two 60 cm TSK G4000-SW columns in series (separation range 5 kD-1000 kD), by elution with 0.1M Tris-HCl buffer pH 7.4 at 1 ml per min. The active glycoprotease fraction was re-chromatographed by anionexchange HPLC on a MonoQ HR 5/5 column, with a gradient of 0–0.5M NaCl eluted at i ml per min. This yielded a single peak of glycoprotease activity, which on SDS-PAGE analysis showed a protein band at $M_T$ 35 kD.

Immobilization of the glycoprotease:

Three pieces of nitrocellulose paper 1 cm² were soaked in 50 mM HEPES buffer, pH 7.4 for 10 min and transferred to a concentrated serum-free preparation of the enzyme, with gentle shaking for 30 min at 4° C. The immobilized enzyme was blocked with 1% hen ovalbumin for 1 h and washed with HEPES buffer for 30 min with five changes of buffer. Characterization of the products of glycophorin hydrolysis by the *P. haemolytica* A1 glycoprotease:

Human erythrocyte ghosts were prepared from outdated pooled blood-bank human blood (Blumenfeld, O.O, P. M. Gallup, and T. H. Liao. 1972. Modification and Introduction of a Specific Radiolabel into the Erythrocyte Membrane Sialoglycoproteins. *Biochem. Biophs. Res. Commun.* 48:242–251) and glycophorin A was extracted (Marchesi, V. T. H. Furthmayr, and M. Tomita. 1976. The Red Cell Membrane. *Ann. Rev. Biochem.* 45:667–678. Glycophorin A was further purified by chromatography on an agarose-wheat germ lectin affinity column (Pharmacia). For some experiments the glycophorin A was radio-iodinated by the method of Markwell (Marwell, M. A. K. 1982. A New Solid-State Reagent to Iodinate Proteins. I. Conditions for the Efficient Labelling of Antiserum. *Anal. Biochem.* 125:427–432. To determine the sites of glycophorin cleavage by the glycoprotease, 70–180 µg of [$_{125}$I]-glycophorin A (60,000) c.p.m.) incubated in 0.5 ml 50 mM Hepes buffer pH 7.4 with 3 cm² of the immobilized enzyme on nitrocellulose, prepared as described above. Incubation was for 3 h and for 18 h at 37° C. The extent of glycophorin hydrolysis was determined by SDS-PAGE analysis of radiolabelled products. Sites of cleavage of the glycophorin were determined by N-terminal amino-acid sequence analysis of the lyophilized products, by the Edman procedure on a gas phase microsequencer (HSC Biotechnology Centre, Toronto).

Electrophoresis:

Enzyme fractions from gel-filtration and ion-exchange chromatography, and products of the digestion of radio-labelled glycophorin by *P. haemolytica* A1 protease, were examined by SDS-PAGE (Laemmli, U. K. 1970. Cleavage of Structural Proteins During Assembly of the Head of Bacteriophage T4. *Nature* (London) 227:680–685). The gels were fixed with 45% ethanol containing 5% glacial acetic acid, washed with water, and stained either with Coomassie blue R250, with silver-staining or with "Stains-all" (Biorad, Mississauga, ON). The latter stain shows the presence of sialoglycoproteins by a blue colour; non-sialylated proteins are stained red. The position of $^3$H-sialyl-glycoproteins on the gels was carried out by fluorography by soaking the gels in scintillator fluid (En$^3$Hance; NEN Canada, Dorval, QU). For fluorography or autoradiography, the dried gels were overlaid with X-ray film (XOMat, Kodak, Toronto, ON) and kept at −70° C. for 6 days in the dark, before development.

Enzyme assays:

The *P. haemolytica* A1 protease was assayed by the hyrolysis of [$^3$H]-sialyl-glycproteins labelled in situ in human erythrocyte ghost membranes (Blumenfeld et al. supra). Enzyme fractions were incubated with [$^3$H]-sialyl human erythrocyte ghost membrane (0.25 mg protein) in 150 µl 0.1M HEPES buffer, pH 7.4 for one to four hours at 37° C. At the end of the incubation the erythrocyte ghosts were sedimented by centrifugation at 13,000×g for 4 min, and 50 µl supernatant was removed and counted for $^3$H-content by liquid scintillation counting. Controls contained enzyme fractions which had been heat-denatured at 100° C. for 15 minutes. The enzyme activity was measured against [$^3$H]-sialyl-glycophorin and expressed in terms of nmol sialate content of the sialoglycopeptides released. In other assays, isolated glycophorin and other proteins were radio-iodinated with Na$^{125}$I by the method of Markwell (Markwell supra). The cleavage of the enzyme of $^{125}$I-labelled glycophorin A was measured by incubating 5 µg radio-labelled glycophorin, 20 µCi per mg, with enzyme in 0.2 ml 0.1M HEPES buffer, pH 7.4 for one hour at 37° C. The radio-labelled products and uncleaved substrate was separated by SDS-PAGE, and cleavage was estimated by slicing the gels and counting the distribution of radioactivity in a gamma counter. Neuraminidase activity was measured either by use of the fluoroenic substrate, 4-methylumbelliferyl-α-D-N-acetylneuraminate, or by cleavage of sialyllactose. Sialyl-lactose, 0.1 ml 10 mM, was incubated with 0.1 ml enzyme fraction in 0.1M HEPES buffer, pH 7.4, for 4 h at 37° C. The released sialate was assayed by the method of Warren (Tomita, M., H. Furthmayr, and V. T. Marchesi. 1978. Primary Structure of Human Erythrocyte Glycophorin A. Isolation and characterization of peptides and complete amino acid sequence. *Biochemistry* 17:4756–4770. Protein was assayed by the method of Peterson (Peterson, G. L. 1977. A simplification of the protein assay method of Lowry et al. which is more generally applicable. *Anal. Biochem.* 83:346–356.

TABLE 1

Proteolysis of [$^3$H]-sialoglycoprotein of erythrocyte ghosts, compared to macrophase cytotoxicity, for culture supernatant fractions of *P. haemolytica* A1.

| Fraction | Protein mg | Proteolysis cpm/mg protein/h (% recovery) | Cytotoxicity[a] % |
|---|---|---|---|
| 1. Supernatant | 241.5 | 7,000 ± 100 (100) | 100.0 ± 2.6 |
| 2. Dialyzed supernatant | 241.5 | 12,000 ± 300 (171) | 82.0 ± 3.1 |
| 3. pH 4.5-precipitate of (1) | 43.6 | 126,000 ± 2800 (306) | 0 |
| 4. pH 4.5-supernatant of (1) | 195.2 | 0 (0) | 100 ± 3.6 |

TABLE 1-continued

Proteolysis of [$^3$H]-sialoglycoprotein of erythrocyte ghosts, compared to macrophase cytotoxicity, for culture supernatant fractions of *P. haemolytica* A1.

| Fraction | Protein mg | Proteolysis cpm/mg protein/h (% recovery) | Cytotoxicity[a] % |
|---|---|---|---|

[a]Cytotoxicity was measured as the release of [$^{51}$Cr] chromate from bovine pulmonary macrophages (19), mean ± S.E.M., n = 3.

TABLE 2

Isolation of the glycoprotease from serum-free culture supernatant of *P. haemolytica* A1.

| | Glycoprotease | | | | |
|---|---|---|---|---|---|
| | Total Protein (µg) | Total Activity (nmol/h) | Specific Activity (nmol/ mg/h) | Purification fold | % Recovery |
| Ultrafiltration Amicon PM-10 | 100 | 0.050 | 0.5 | — | 100 |
| TSK G4000-SW (Fraction 6) | 28 | 0.042 | 1.5 | 3 | 84 |
| Mono Q HR 5/5 (Fraction 24) | 0.43 | 0.040 | 94.0 | 188 | 80 |

TABLE 3

Effect of inhibitors on the cleavage of soluble [$^{125}$I]-glycophorin A by the *P. haemolytica* Al glycoprotease.

| Inhibitor | Concentration (mM) | Activity[a] (%) |
|---|---|---|
| None | | 100 |
| Phosphoramidon | 0.9 | 95 ± 4 |
| Sialate | 2.5 | 99 ± 1 |
| Citrate | 5.2 | 45 ± 1 |
| Ascorbate | 11.4 | 60 ± 2 |
| EDTA | 0.1 | 95 ± 5 |
| EDTA | 1.0 | 0 |

[a]The serum-free enzyme was pre-incubated with the inhibitor for 30 min at 37° C., pH 7.4, followed by addition of soluble [$^{125}$I]-glycophorin and further incubation for 1 h. The degradation of glycophorin was assayed by SDS-PAGE analysis and autoradiography. The disappearance of glycophorin A dimer was measured by densitometry of the autoradiographs and is expressed as a percentage of enzyme activity in the absence of any inhibitor. Negative controls contained heat-denatured enzyme with each inhibitor tested. Mean ± SD (n = 2).

TABLE 4

Specificity of glycoprotease for peptide bond cleavage of glycophorin A.

| | Site of cleavage[a] | | | |
|---|---|---|---|---|
| Time (b) | $P_1$ | $P_1'$ | Sequence[b] | Amount (pmol)[c] |
| 3 | Arg31 | Asp32 | 32–39 | 9.2 |
| 18 | Glu60 | Ary61 | 61–70 | 38 |
| 18 | Arg31 | Asp32 | 32–39 | 37 |
| 18 | Ala65 | His66 | 66–79 | 14 |
| 18 | Tyr34 | Ala35 | 35–40 | 12 |

[a]$P_1$–$P_1'$ represents the amide bond cleaved.
[b]Glycophorin A amino acid residues identified for new N-terminal sequence.
[c]The amount of cleavage represents the pmol of each new N-terminal sequence, measured for the first amino acid. At both times, the major sequence found was that of the N-terminal region of glycophorin A, from cleaved and uncleaved substrate, and was 37 pmol at 3 h and 93 pmol at 18 h.

We claim:

1. A purified DNA molecule comprising a DNA sequence encoding a glycoprotease having the amino acid sequence shown in SEQ ID NO:2.

2. A purified DNA molecule comprising nucleotides 175–1168 of SEQ ID NO:1, coding for a glycoprotease having a molecular weight of approximately 35.2 kD.

3. A purified DNA molecule comprising at least 18 nucleotides encoding a fragment of a glycoprotease amino acid sequence, said fragment being selected from at least 6 corresponding sequential amino acid residues of said amino acid sequence of SEQ ID NO: 1.

4. A recombinant expression vector comprising a DNA molecule of claim 1.

5. A host cell transformed with a recombinant cloning vector comprising a DNA molecule of claim 1.

6. A host cell of claim 9, wherein said host cell is selected from the group consisting of prokaryotic and eukaryotic cells, said DNA molecule being operatively linked to an expression control sequence so that said glycoprotease is expressed, said expression control sequence being selected from the group consisting of sequences that control the expression of genes of prokaryotic or eucaryotic cells.

7. A process of recombinantly producing a glycoprotease, comprising culturing the host cell of claim 5.

8. A process of recombinantly producing a glycoprotease, comprising culturing a host cell transformed with a recombinant expression vector comprising the DNA of claim 2.

9. The process of claim 7, further comprising separating said glycoprotease from said culture medium and purifying said glycoprotease.

10. The process of claim 7, wherein said host cell is *Escherichia coli*.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1315 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS
        ( B ) LOCATION: 141..1115

( x i ) SEQUENCE DESCRIPTION: SEQ ID NO:1:

```
GGATCCAAGA  ATATGAAAGC  AAAGAGCTAC  CGAATCCTGA  AAAACTGAAG  TATGGCGAAC        60

AATTCTAGTC  GTACAGAGAA  TAATGTGAGG  GGCGTTCTTC  GCCCCTTTTG  GTTTTCTAAC       120

TTATTTTGAC  TTCTCCAACT  ATG CGA ATT TTA GGT ATT GAA ACC TCT TGT             170
                       Met Arg Ile Leu Gly Ile Glu Thr Ser Cys
                         1               5                  10

GAT GAA ACC GGT GTT GCC ATT TAT GAT GAA GAC AAA GGC TTA GTG GCA             218
Asp Glu Thr Gly Val Ala Ile Tyr Asp Glu Asp Lys Gly Leu Val Ala
                15                  20                  25

AAC CAG CTT TAT AGC CAA ATT GAT ATG CAC GCC GAT TAC GGT GGC GTA             266
Asn Gln Leu Tyr Ser Gln Ile Asp Met His Ala Asp Tyr Gly Gly Val
            30                  35                  40

GTC CCT GAA CTG GCT TCT CGA GAC CAT ATC CGT AAA ACG TTG CCA CTA             314
Val Pro Glu Leu Ala Ser Arg Asp His Ile Arg Lys Thr Leu Pro Leu
        45                  50                  55

ATT CAA GAA GCC TTA AAA GAG GCC AAT CTG CAA CCC TCG GAT ATT GAC             362
Ile Gln Glu Ala Leu Lys Glu Ala Asn Leu Gln Pro Ser Asp Ile Asp
    60                  65                  70

GGC ATT GCC TAT ACT GCC GGC CCA GGC TTG GTC GGG GCT TTA TTG GTC             410
Gly Ile Ala Tyr Thr Ala Gly Pro Gly Leu Val Gly Ala Leu Leu Val
75                  80                  85                  90

GGC TCA ACC ATT GCC CGT TCG CTG GCT TAT GCT TGG AAT GTT CCG GCA             458
Gly Ser Thr Ile Ala Arg Ser Leu Ala Tyr Ala Trp Asn Val Pro Ala
                95                 100                 105

TTG GGC GTT CAC CAT ATG GAA GGG CAT TTA CTT GCC CCA ATG TTG GAA             506
Leu Gly Val His His Met Glu Gly His Leu Leu Ala Pro Met Leu Glu
            110                 115                 120

GAA AAT GCC CCT GAA TTT CCG TTT GTG GCA TTA TTG ATT TCA GGT GGA             554
Glu Asn Ala Pro Glu Phe Pro Phe Val Ala Leu Leu Ile Ser Gly Gly
        125                 130                 135

CAC ACC CAA CTG GTA AAA GTT GAC GGC GTT GGG CAA TAC GAA CTA CTC             602
His Thr Gln Leu Val Lys Val Asp Gly Val Gly Gln Tyr Glu Leu Leu
    140                 145                 150

GGG GAA TCA ATT GAT GAT GCT GCC GGT GAA GCC TTT GAC AAA ACA GGC             650
Gly Glu Ser Ile Asp Asp Ala Ala Gly Glu Ala Phe Asp Lys Thr Gly
155                 160                 165                 170

AAA CTA CTC GGT TTG GAT TAC CCT GCC GGT GTA GCG ATG TCA AAA TTA             698
Lys Leu Leu Gly Leu Asp Tyr Pro Ala Gly Val Ala Met Ser Lys Leu
                175                 180                 185
```

| | | | | | | | | | | | | | | | | |
|---|---|---|---|---|---|---|---|---|---|---|---|---|---|---|---|---|
| GCC | GAA | TCC | GGC | ACG | CCA | AAT | CGT | TTT | AAA | TTC | CCT | CGT | CCA | ATG | ACC | 746 |
| Ala | Glu | Ser | Gly | Thr | Pro | Asn | Arg | Phe | Lys | Phe | Pro | Arg | Pro | Met | Thr | |
| | | | 190 | | | | | 195 | | | | | 200 | | | |
| GAC | AGA | CCG | GGA | CTG | GAT | TTC | AGT | TTC | TCC | GGT | TTA | AAA | ACC | TTT | GCT | 794 |
| Asp | Arg | Pro | Gly | Leu | Asp | Phe | Ser | Phe | Ser | Gly | Leu | Lys | Thr | Phe | Ala | |
| | | 205 | | | | | | 210 | | | | | 215 | | | |
| GCG | AAT | ACG | ATT | AAA | GCC | AAT | CTT | AAT | GAA | AAT | GGT | GAA | CTC | GAT | GAG | 842 |
| Ala | Asn | Thr | Ile | Lys | Ala | Asn | Leu | Asn | Glu | Asn | Gly | Glu | Leu | Asp | Glu | |
| | | 220 | | | | | 225 | | | | | 230 | | | | |
| CAA | ACC | AAA | TGC | GAT | ATT | GCC | CAC | GCA | TTC | CAA | CAA | GCC | GTG | GTT | GAT | 890 |
| Gln | Thr | Lys | Cys | Asp | Ile | Ala | His | Ala | Phe | Gln | Gln | Ala | Val | Val | Asp | |
| 235 | | | | | 240 | | | | | 245 | | | | | 250 | |
| ACT | ATT | TTA | ATT | AAA | TGC | AAG | CGA | GCG | TTA | GAG | CAA | ACC | GGC | TAT | AAA | 938 |
| Thr | Ile | Leu | Ile | Lys | Cys | Lys | Arg | Ala | Leu | Glu | Gln | Thr | Gly | Tyr | Lys | |
| | | | | 255 | | | | | 260 | | | | | 265 | | |
| CGC | TTA | GTA | ATG | GCA | GGC | GGC | GTA | AGT | GCC | AAT | AAA | CAA | TTA | CGA | GCA | 986 |
| Arg | Leu | Val | Met | Ala | Gly | Gly | Val | Ser | Ala | Asn | Lys | Gln | Leu | Arg | Ala | |
| | | | 270 | | | | | 275 | | | | | 280 | | | |
| GAC | CTT | GCG | GAA | ATG | ATG | AAA | AAA | TTA | AAA | GGC | GAA | GTA | TTC | TAC | CCT | 1034 |
| Asp | Leu | Ala | Glu | Met | Met | Lys | Lys | Leu | Lys | Gly | Glu | Val | Phe | Tyr | Pro | |
| | | 285 | | | | | 290 | | | | | 295 | | | | |
| CGC | CCA | CAA | TTT | TGC | ACT | GAC | AAC | GGC | GCA | ATG | ATT | GCC | TAC | ACT | GGC | 1082 |
| Arg | Pro | Gln | Phe | Cys | Thr | Asp | Asn | Gly | Ala | Met | Ile | Ala | Tyr | Thr | Gly | |
| | 300 | | | | | 305 | | | | | 310 | | | | | |
| TTT | CTT | CGC | TTA | AAA | ACG | ATG | AAC | AAA | CCG | ACT | TAAGCATTAG | | CGTAAACCCC | | | 1135 |
| Phe | Leu | Arg | Leu | Lys | Thr | Met | Asn | Lys | Pro | Thr | | | | | | |
| 315 | | | | | 320 | | | | | 325 | | | | | | |

GCTGGCTATG ACCGAATTAC CACCGATTAA TTAACCTTTC AAGCGGTGAA ATTTCTTGTT 1195

AATTTTGCAA AAATTTAATC AAAAATAACC GCTTGCTATA TGATAGATTA AATTTATGAA 1255

TAATTATGTA ATTAGCCTAC CTCCGCACAG GAGCGTAGAA AACATATTCA AGCTGAATTC 1315

( 2 ) INFORMATION FOR SEQ ID NO:2:

( i ) SEQUENCE CHARACTERISTICS:
        ( A ) LENGTH: 325 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Met | Arg | Ile | Leu | Gly | Ile | Glu | Thr | Ser | Cys | Asp | Glu | Thr | Gly | Val | Ala |
| 1 | | | | 5 | | | | | 10 | | | | | 15 | |
| Ile | Tyr | Asp | Glu | Asp | Lys | Gly | Leu | Val | Ala | Asn | Gln | Leu | Tyr | Ser | Gln |
| | | | 20 | | | | | 25 | | | | | 30 | | |
| Ile | Asp | Met | His | Ala | Asp | Tyr | Gly | Gly | Val | Val | Pro | Glu | Leu | Ala | Ser |
| | | 35 | | | | | 40 | | | | | 45 | | | |
| Arg | Asp | His | Ile | Arg | Lys | Thr | Leu | Pro | Leu | Ile | Gln | Glu | Ala | Leu | Lys |
| | 50 | | | | | 55 | | | | | 60 | | | | |
| Glu | Ala | Asn | Leu | Gln | Pro | Ser | Asp | Ile | Asp | Gly | Ile | Ala | Tyr | Thr | Ala |
| 65 | | | | | 70 | | | | | 75 | | | | | 80 |
| Gly | Pro | Gly | Leu | Val | Gly | Ala | Leu | Leu | Val | Gly | Ser | Thr | Ile | Ala | Arg |
| | | | | 85 | | | | | 90 | | | | | 95 | |
| Ser | Leu | Ala | Tyr | Ala | Trp | Asn | Val | Pro | Ala | Leu | Gly | Val | His | His | Met |
| | | | 100 | | | | | 105 | | | | | 110 | | |
| Glu | Gly | His | Leu | Leu | Ala | Pro | Met | Leu | Glu | Glu | Asn | Ala | Pro | Glu | Phe |
| | | 115 | | | | | 120 | | | | | 125 | | | |
| Pro | Phe | Val | Ala | Leu | Leu | Ile | Ser | Gly | Gly | His | Thr | Gln | Leu | Val | Lys |
| | 130 | | | | | 135 | | | | | 140 | | | | |

```
Val Asp Gly Val Gly Gln Tyr Glu Leu Leu Gly Glu Ser Ile Asp Asp
145                 150                 155                 160

Ala Ala Gly Glu Ala Phe Asp Lys Thr Gly Lys Leu Leu Gly Leu Asp
            165                 170                 175

Tyr Pro Ala Gly Val Ala Met Ser Lys Leu Ala Glu Ser Gly Thr Pro
            180                 185                 190

Asn Arg Phe Lys Phe Pro Arg Pro Met Thr Asp Arg Pro Gly Leu Asp
        195                 200                 205

Phe Ser Phe Ser Gly Leu Lys Thr Phe Ala Ala Asn Thr Ile Lys Ala
    210                 215                 220

Asn Leu Asn Glu Asn Gly Glu Leu Asp Glu Gln Thr Lys Cys Asp Ile
225                 230                 235                 240

Ala His Ala Phe Gln Gln Ala Val Val Asp Thr Ile Leu Ile Lys Cys
            245                 250                 255

Lys Arg Ala Leu Glu Gln Thr Gly Tyr Lys Arg Leu Val Met Ala Gly
            260                 265                 270

Gly Val Ser Ala Asn Lys Gln Leu Arg Ala Asp Leu Ala Glu Met Met
        275                 280                 285

Lys Lys Leu Lys Gly Glu Val Phe Tyr Pro Arg Pro Gln Phe Cys Thr
        290                 295                 300

Asp Asn Gly Ala Met Ile Ala Tyr Thr Gly Phe Leu Arg Leu Lys Thr
305                 310                 315                 320

Met Asn Lys Pro Thr
                325

( 2 ) INFORMATION FOR SEQ ID NO:3:

( i ) SEQUENCE CHARACTERISTICS:
                ( A ) LENGTH: 342 amino acids
                ( B ) TYPE: amino acid
                ( C ) STRANDEDNESS: single
                ( D ) TOPOLOGY: linear ( i i ) MOLECULE TYPE: peptide ( x i ) SEQUENCE DESCRIPTION: SEQ ID NO:3:

Met Arg Val Leu Gly Ile Glu Thr Ser Cys Asp Glu Thr Gly Ile Ala
1               5                   10                  15

Ile Tyr Asp Asp Glu Lys Gly Leu Leu Ala Asn Gln Leu Tyr Ser Gln
            20                  25                  30

Val Lys Leu His Ala Asp Tyr Gly Gly Val Val Pro Glu Leu Ala Ser
        35                  40                  45

Arg Asp His Val Arg Lys Thr Val Pro Leu Ile Gln Ala Ala Leu Lys
    50                  55                  60

Glu Ser Gly Leu Thr Ala Lys Asp Ile Asp Ala Val Ala Tyr Thr Ala
65                  70                  75                  80

Gly Pro Gly Leu Val Gly Ala Leu Leu Val Gly Ala Thr Val Gly Arg
            85                  90                  95

Ser Leu Ala Phe Ala Trp Asp Val Pro Ala Ile Pro Val His His Met
            100                 105                 110

Glu Gly His Leu Leu Ala Pro Met Leu Glu Asp Asn Pro Pro Glu Phe
        115                 120                 125

Pro Phe Val Ala Leu Leu Val Ser Gly Gly His Thr Gln Leu Ile Ser
    130                 135                 140

Val Thr Gly Ile Gly Gln Tyr Glu Leu Leu Gly Glu Ser Ile Asp Asp
145                 150                 155                 160
```

| | | | | | | | | | | | | | | | |
|---|---|---|---|---|---|---|---|---|---|---|---|---|---|---|---|
| Ala | Ala | Gly | Glu | Ala 165 | Phe | Asp | Lys | Thr 170 | Lys | Leu | Leu | Gly | Leu 175 | Asp | |
| Tyr | Pro | Gly | Gly 180 | Pro | Leu | Leu | Ser | Lys 185 | Met | Ala | Ala | Gln | Gly 190 | Thr | Ala |
| Gly | Arg | Phe 195 | Val | Phe | Pro | Arg | Pro 200 | Met | Thr | Asp | Arg | Pro 205 | Gly | Leu | Asp |
| Phe | Ser 210 | Phe | Ser | Gly | Leu | Lys 215 | Thr | Phe | Ala | Ala | Asn 220 | Thr | Ile | Arg | Asp |
| Asn 225 | Xaa | Xaa | Xaa | Xaa | Gly 230 | Xaa | Thr | Asp | Asp | Gln 235 | Thr | Arg | Ala | Asp | Ile 240 |
| Ala | Arg | Ala | Phe | Glu 245 | Asp | Ala | Val | Val | Asp 250 | Thr | Leu | Met | Ile | Lys 255 | Cys |
| Lys | Arg | Ala | Leu 260 | Asp | Gln | Thr | Gly | Phe 265 | Lys | Arg | Leu | Val | Met 270 | Ala | Gly |
| Gly | Val | Ser 275 | Ala | Asn | Arg | Thr | Leu 280 | Arg | Ala | Lys | Leu | Ala 285 | Glu | Met | Met |
| Lys | Lys 290 | Arg | Arg | Gly | Glu | Val 295 | Phe | Tyr | Ala | Arg | Pro 300 | Glu | Phe | Cys | Thr |
| Asp 305 | Asn | Gly | Ala | Met | Ile 310 | Ala | Tyr | Ala | Gly | Met 315 | Val | Arg | Phe | Lys | Ala 320 |
| Gly | Ala | Thr | Ala | Asp 325 | Leu | Gly | Val | Ser | Val 330 | Arg | Pro | Arg | Trp | Pro 335 | Leu |
| Ala | Glu | Leu | Pro 340 | Ala | Ala | | | | | | | | | | |